US011236303B2

United States Patent
Strassel et al.

(10) Patent No.: US 11,236,303 B2
(45) Date of Patent: Feb. 1, 2022

(54) CD34+CD41$^{DIM}$ MEGAKARYOCYTES PROGENITORS AND USES THEREOF FOR PRODUCING PROPLATELET-BEARING MKS AND/OR PLATELETS

(71) Applicants: INSTITUT NATIONAL DE LA SANTE ET DE LA RECHERCHE MEDICALE (INSERM), Paris (FR); Etablissement Français du Sang, La Plaine Saint Denis (FR)

(72) Inventors: Catherine Strassel, Strasbourg (FR); Christian Gachet, Lalaye (FR); François Lanza, Beinheim (FR); Nathalie Brouard, Strasbourg (FR)

(73) Assignees: INSTITUT NATIONAL DE LA SANTE ET DE LA RECHERCHE MEDICALE (INSERM), Paris (FR); ETABLISSMENT FRANçIS DU SANG, La Plaine Saint Denis (FR); UNIVERSITÉ DE STRASBOURG, Strasbourg (FR)

( * ) Notice: Subject to any disclaimer, the term of this patent is extended or adjusted under 35 U.S.C. 154(b) by 420 days.

(21) Appl. No.: 15/747,023

(22) PCT Filed: Jul. 22, 2016

(86) PCT No.: PCT/EP2016/067594
§ 371 (c)(1),
(2) Date: Jan. 23, 2018

(87) PCT Pub. No.: WO2017/013262
PCT Pub. Date: Jan. 26, 2017

(65) Prior Publication Data
US 2018/0216068 A1  Aug. 2, 2018

(30) Foreign Application Priority Data

Jul. 23, 2015 (FR) .................................. 15 57020

(51) Int. Cl.
*C12N 5/078* (2010.01)

(52) U.S. Cl.
CPC ........ *C12N 5/0644* (2013.01); *C12N 2500/25* (2013.01); *C12N 2500/36* (2013.01);
(Continued)

(58) Field of Classification Search
CPC .......... C12N 5/0644; C12N 2501/2309; C12N 2501/125; C12N 2506/11; C12N 2501/60;
(Continued)

(56) References Cited

U.S. PATENT DOCUMENTS 7,494,807 B2    2/2009 Nakorn et al.
9,074,186 B2    7/2015 Murphy et al.
(Continued)

FOREIGN PATENT DOCUMENTS

WO    WO-2009119105    7/2011
WO    WO-2014138485    9/2014
WO    WO-2017013262    1/2017

OTHER PUBLICATIONS

Deutsch et al, Mimicking the haematopoietic niche microenvironment provides a novel strategy for expansion of haematopoietic and megakaryocyte-progenitor cells from cord blood 2010, British Journal of Haematology, 149:137-149 (Year: 2010).*

(Continued)

*Primary Examiner* — Sean C. Barron
(74) *Attorney, Agent, or Firm* — B. Aaron Schulman, Esq.; Stites & Harbison, PLLC

(57) ABSTRACT

The invention relates to a method of producing CD34+CD4$^{dim}$ megakaryocyte (MK) progenitor cells, and substantially pure cell population of megakaryocyte precursor cells obtained by said method. The invention also relates to a method of producing proplatelet-bearing MKs and/or platelets using the CD34+CD4$^{dim}$ cells.

15 Claims, 12 Drawing Sheets

Figure 2:
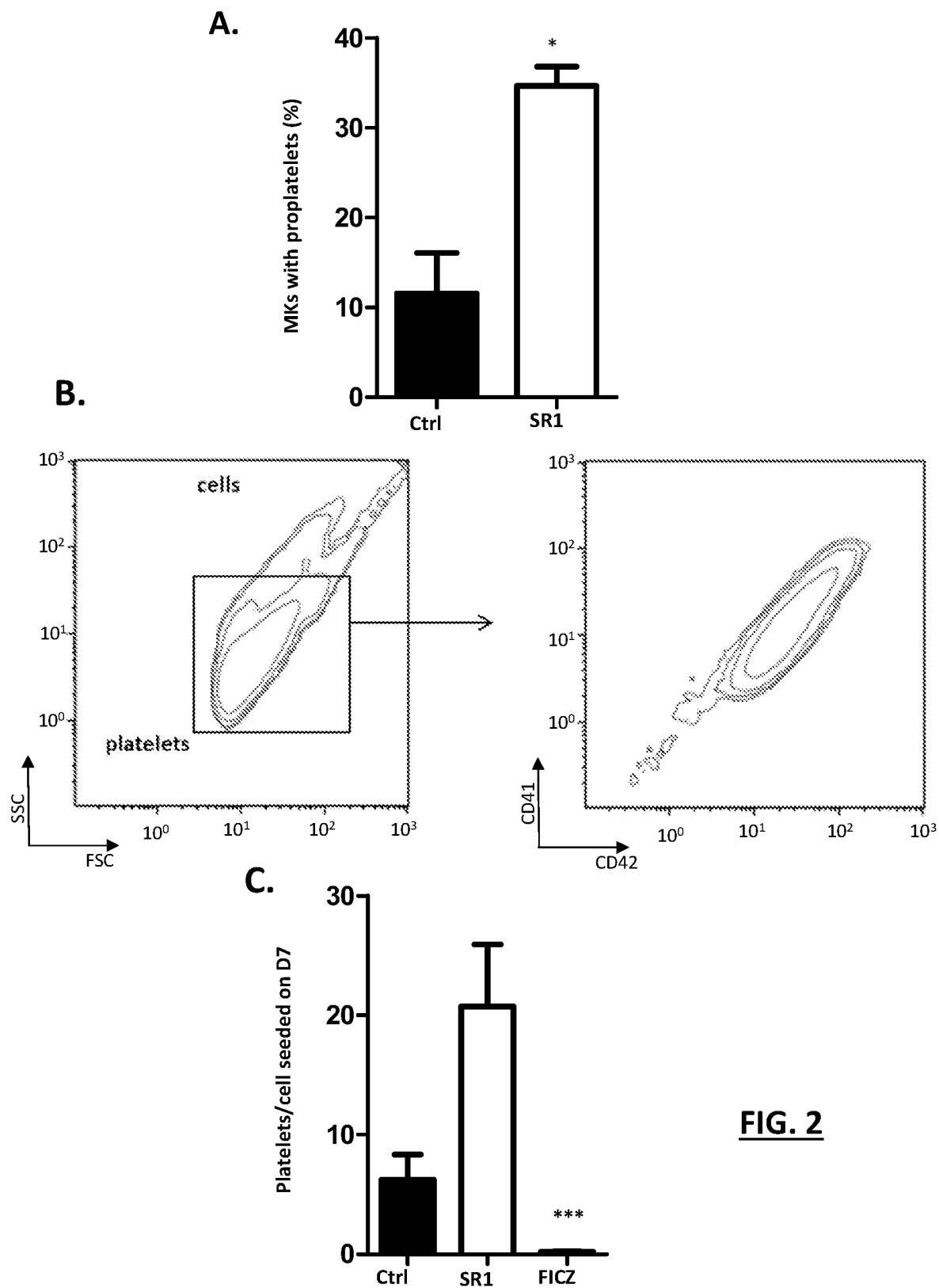

(52) U.S. Cl.
CPC .... *C12N 2500/90* (2013.01); *C12N 2501/125* (2013.01); *C12N 2501/145* (2013.01); *C12N 2501/2306* (2013.01); *C12N 2501/2309* (2013.01); *C12N 2501/60* (2013.01); *C12N 2501/999* (2013.01); *C12N 2502/1358* (2013.01); *C12N 2506/11* (2013.01)

(58) Field of Classification Search
CPC ........ C12N 2500/36; C12N 2502/1358; C12N 2500/90; C12N 2501/145; C12N 2500/25; C12N 2501/999; C12N 2501/2306; A61P 7/08
See application file for complete search history.

(56) References Cited

U.S. PATENT DOCUMENTS

| | | |
|---|---|---|
| 9,574,178 B2 | 2/2017 | Beau et al. |
| 9,896,660 B2 | 2/2018 | Murphy et al. |
| 9,919,009 B2 | 3/2018 | Murphy et al. |
| 10,544,393 B2 | 1/2020 | Murphy et al. |
| 2005/0176142 A1 | 8/2005 | Nakorn et al. |
| 2013/0216506 A1 | 1/2013 | Arbell |
| 2014/0050711 A1 | 2/2014 | Murphy et al. |
| 2015/0203819 A1 | 7/2015 | Murphy et al. |
| 2015/0335680 A1 | 11/2015 | Murphy et al. |
| 2015/0335682 A1 | 11/2015 | Murphy et al. |
| 2018/0291344 A1 | 10/2018 | Murphy et al. |

OTHER PUBLICATIONS

Boitano et al. Aryl Hydrocarbon Receptor Antagonists Promote the Expansion of Human Hematopoietic Stem Cells. Science (2010), 329, 1345-1348. (Year: 2010).*

Pineault et al. Ex Vivo Differentiation of Cord Blood Stem Cells into Megakaryocytes and Platelets. Chapter 13 in Methods in Molecular Biology (2013), 946, 205-224. (Year: 2013).*

Cheng et al. Human Mesenchymal Stem Cells Support Megakaryocyte and Pro-Platelet Formation From CD34+ Hematopoietic Progenitor Cells. Journal of Cellular Physiology (2000), 184, 58-69. (Year: 2000).*

Clay et al. CD9 and megakaryocyte differentiation. Blood (2001), 97, 1982-1989. (Year: 2001).*

Otani et al. Progenitor analysis of primitive erythropoiesis generated from in vitro culture of embryonic stem cells. Experimental Hematology (2005), 33, 632-640. (Year: 2005).*

Ferkowicz et al. CD41 expression defines the onset of primitive and definitive hematopoiesis in the murine embryo. Development (2003), 130, 4393-4403. (Year: 2003).*

Heinz et al. Use of CD9 expression to enrich for porcine hematopoietic progenitors. Experimental Hematology (2002), 30, 809-815. (Year: 2002).*

Liu B et al: "A potential activity of valproic acid in the stimulation of interleukin-3-mediated megakaryopoiesis and erythropoiesis", Experimental Hematology, Elsevier Inc, US, vol. 38, No. 8, Aug. 1, 2010 (Aug. 1, 2010), pp. 685-695, XP027136852, ISSN: 0301-472X [retrieved on Apr. 8, 2010] the whole document.

McGrath Kathleen E Ed—Sanchez Ana et al: "Utilization of imaging flow cytometry to define intermediates of megakaryopoiesis in vivo and in vitro", Journal of Immunological Methods, vol. 423, Mar. 17, 2015 (Mar. 17, 2015), pp. 45-51, XP029247220, ISSN: 0022-1759, DOI: 10.1016/J.JIM.2015.03.002 the whole document.

Bruno S et al: "In Vitro and In Vivo Megakaryocyte Differentiation of Fresh and E-Vivo Expanded Cord Blood Cells: Rapid and Transient Megakaryocyte Reconstitution", Haematologica, The Hematology Journal: Official Organ of the European Hematology Association, Fondazione Ferrata Storti, IT, vol. 88, No. 4, Apr. 1, 2003 (Apr. 1, 2013), pp. 379-387, XP008077211, ISSN: 0390-6078 the whole document.

L. Cheng et al: "Human Mesenchymal Stem Cells Support Megakaryocyte and Pro-Platelet Formation From CD34 Hematopoietic Progenitor Cells", J. Cell. Physiol., Jan. 1, 2000 (Jan. 1, 2000), pp. 58-69, XP055135575, Retrieved from the Internet: URL:http://onlinelibrary.wiley.com/store/10.1002/(SICI)1097-4652(200007)184:1<58::AI D-JCP6>3.0.00;2-13/asset/6ftp.pdf?v=1&t=hz 20a8j7&3:937389292d034b0fb93b3f66ff525d5eaad37f5c [retrieved on Aug. 20, 2014] cited in the application the whole document.

Dumon S et al: "Differentiation of murine committed megakaryocytic progenitors isolated by a novel strategy reveals the complexity of GATA and Ets factor involvement in megakaryocytopoiesis and an unexpected potential role for GATA-6", Experimental Hematology, Elsevier Inc, US, vol. 34, No. 5, May 1, 2006 (May 1, 2006), pp. 654-663, XP027879560, ISSN: 0301-472X [retrieved on May 1, 2006] the whole document.

International Search Report for PCT/EP2016/067594, dated Oct. 20, 2016.

Written Opinion of the International Searching Authority for PCT/EP2016/067594, dated Oct. 20, 2016.

Preliminary Search Report for FR 1557020, dated Apr. 20, 2016.

* cited by examiner

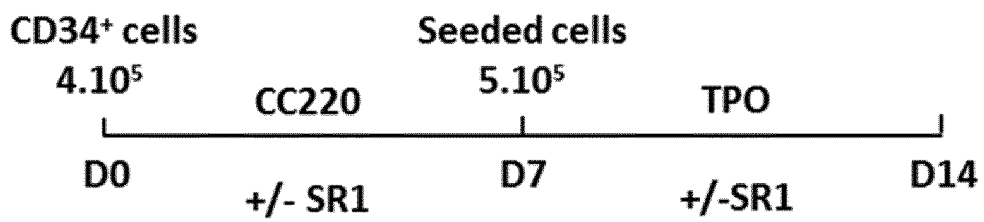
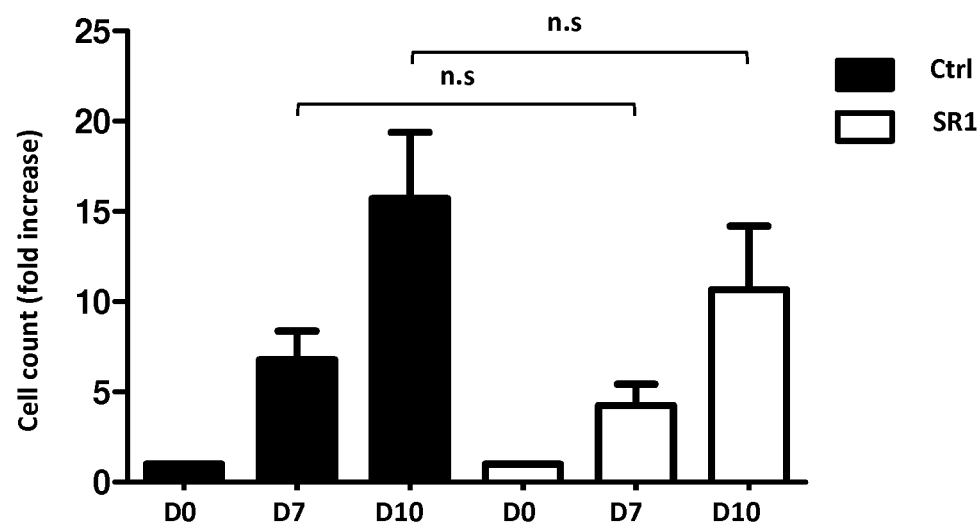
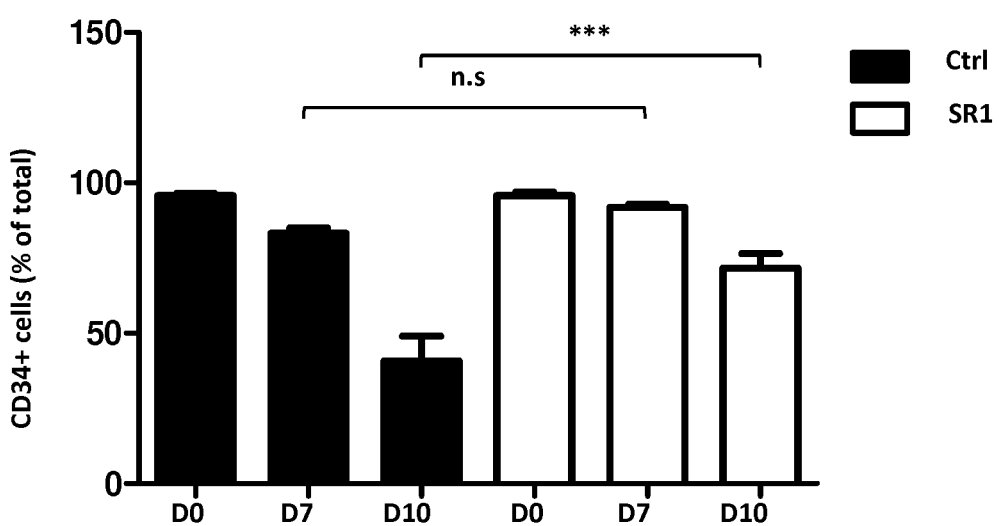
FIG. 1

A.
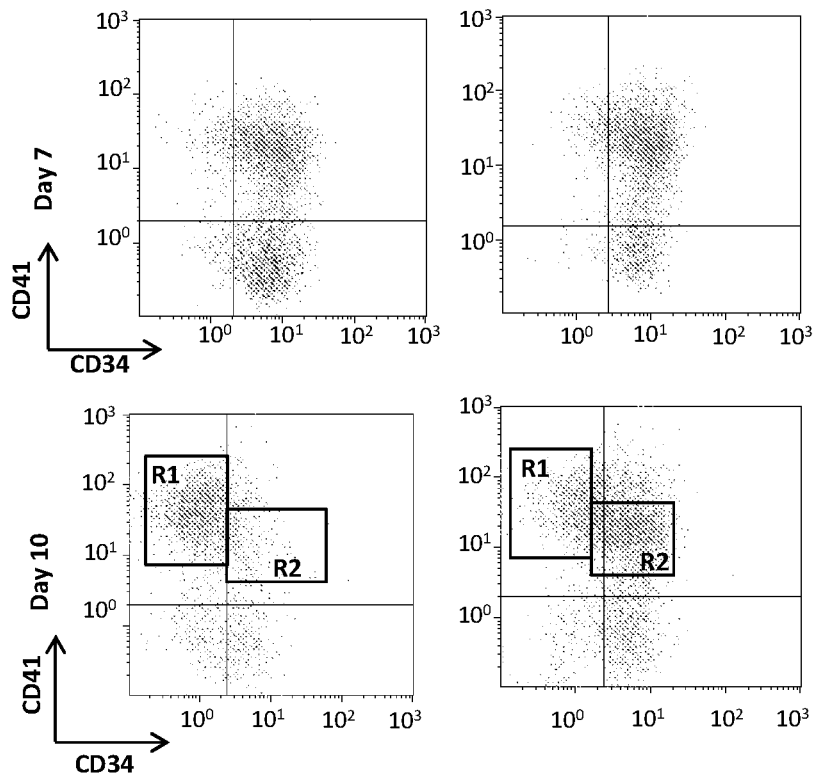
B.
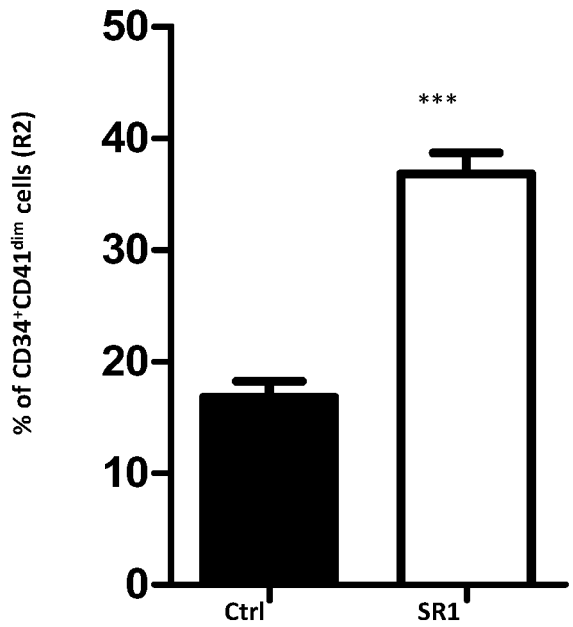
FIG. 3 (Beginning)

C.
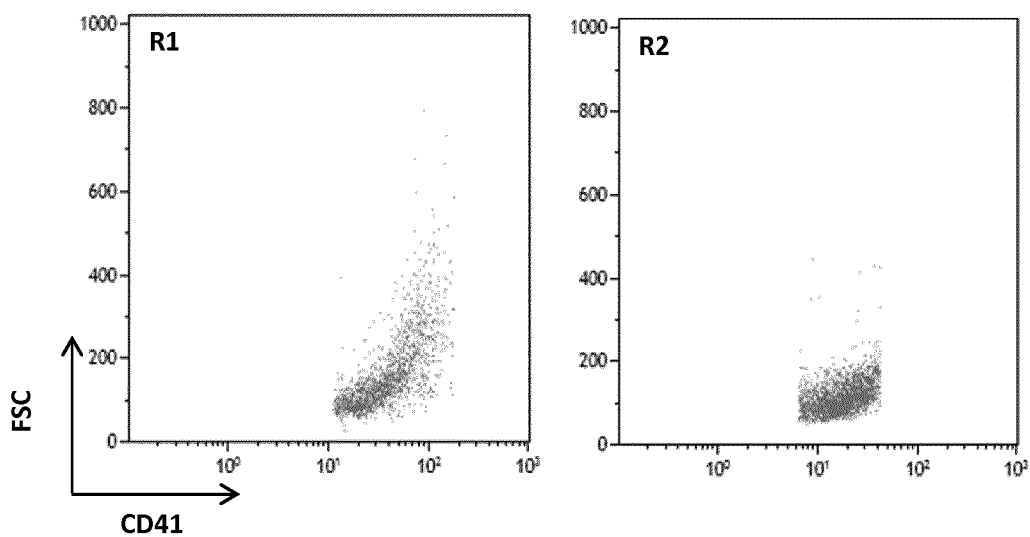
FIG. 3 (End)
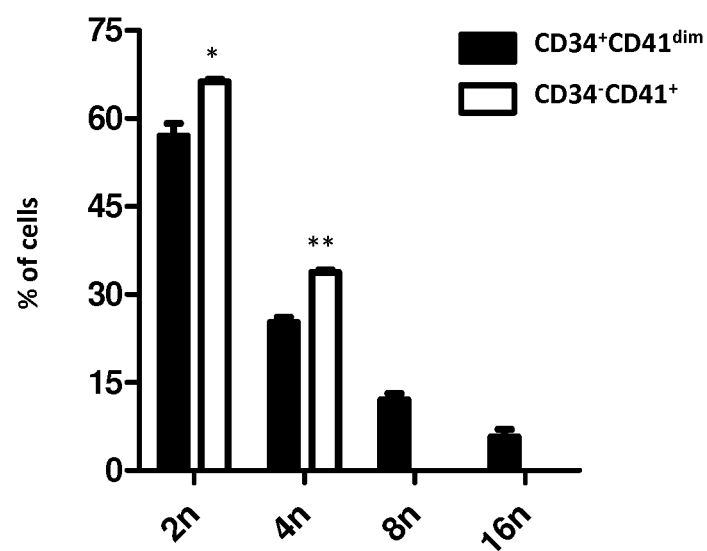
FIG. 4

A.
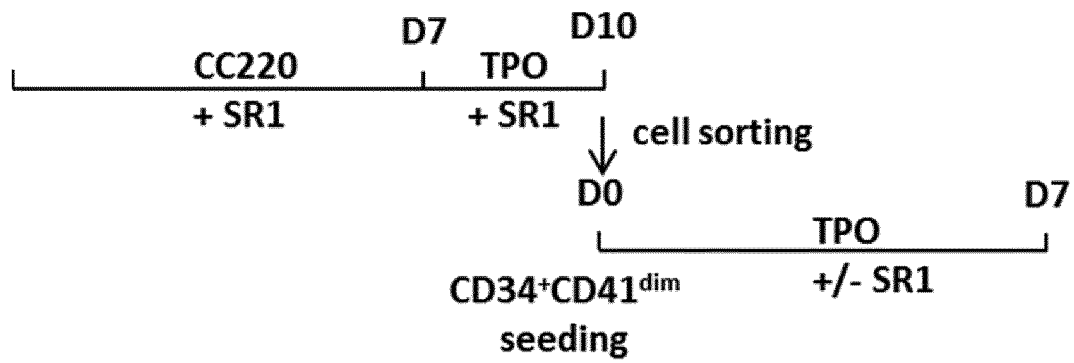
B.
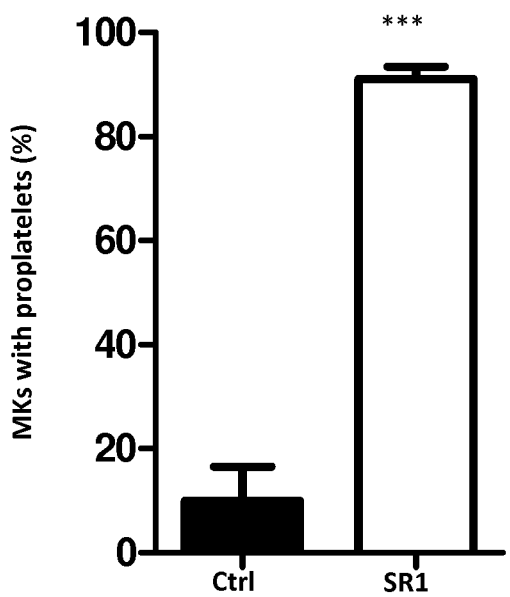
FIG. 5
C.
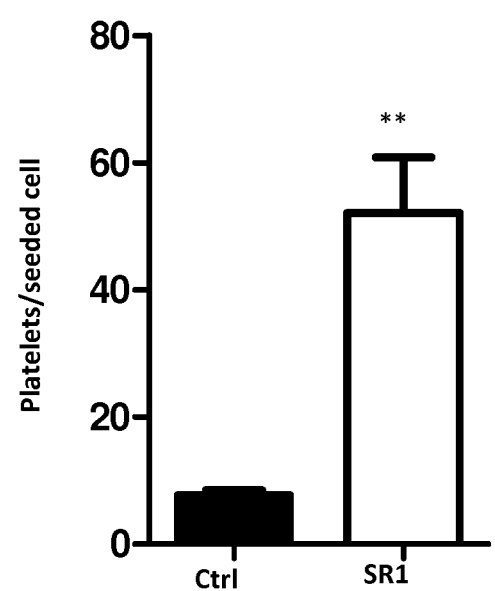

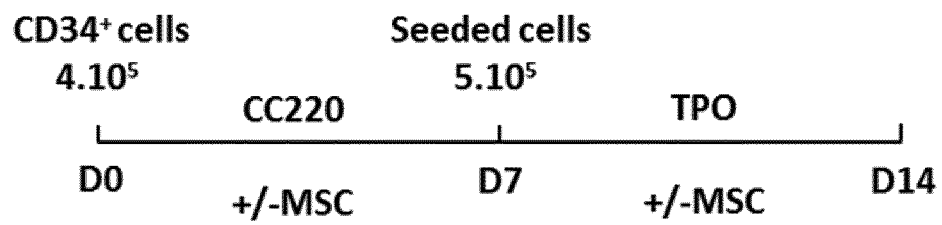
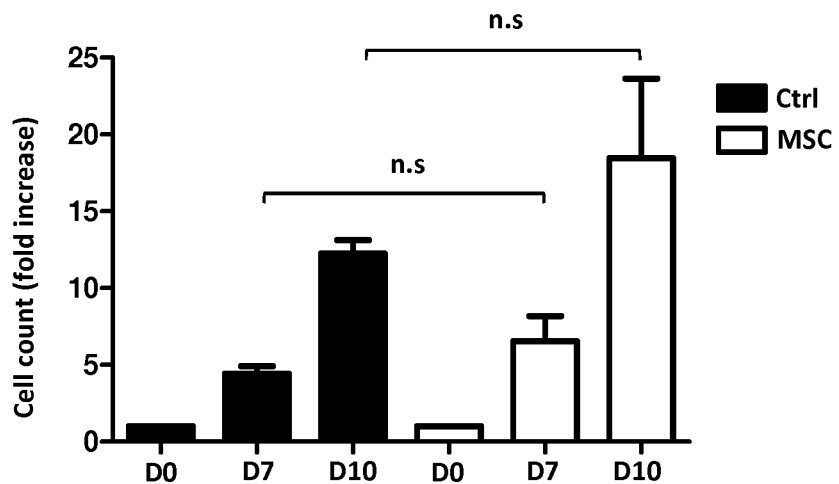
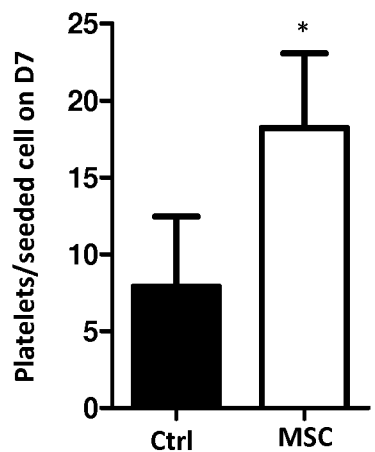
FIG. 6

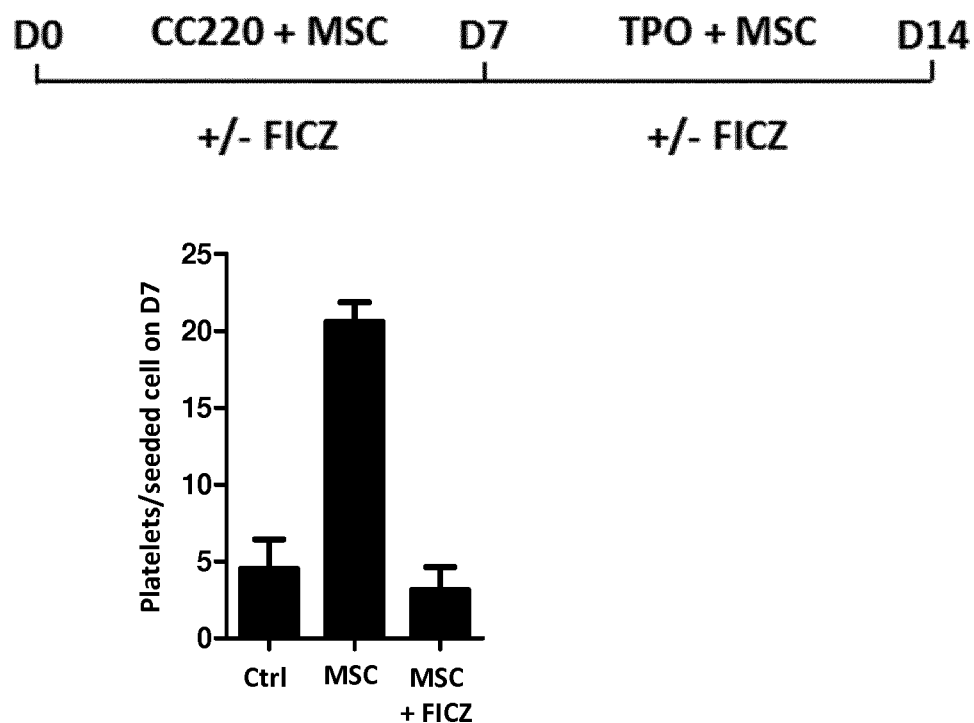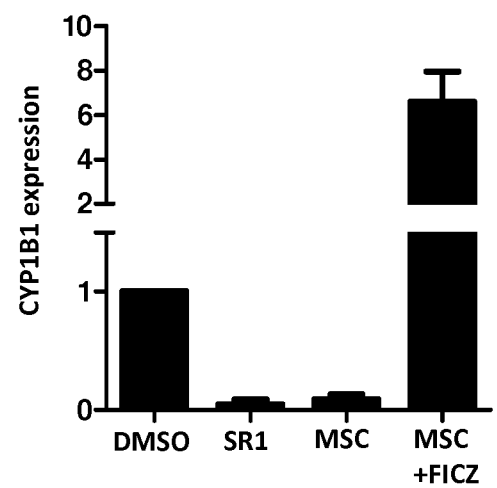
FIG. 7

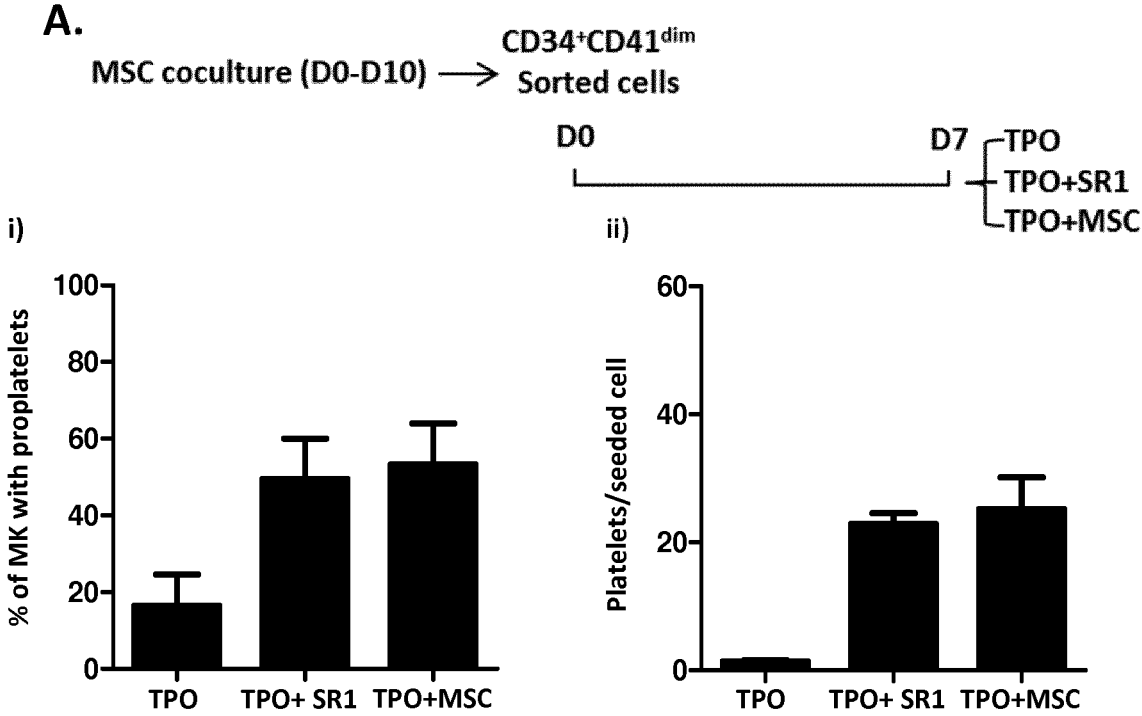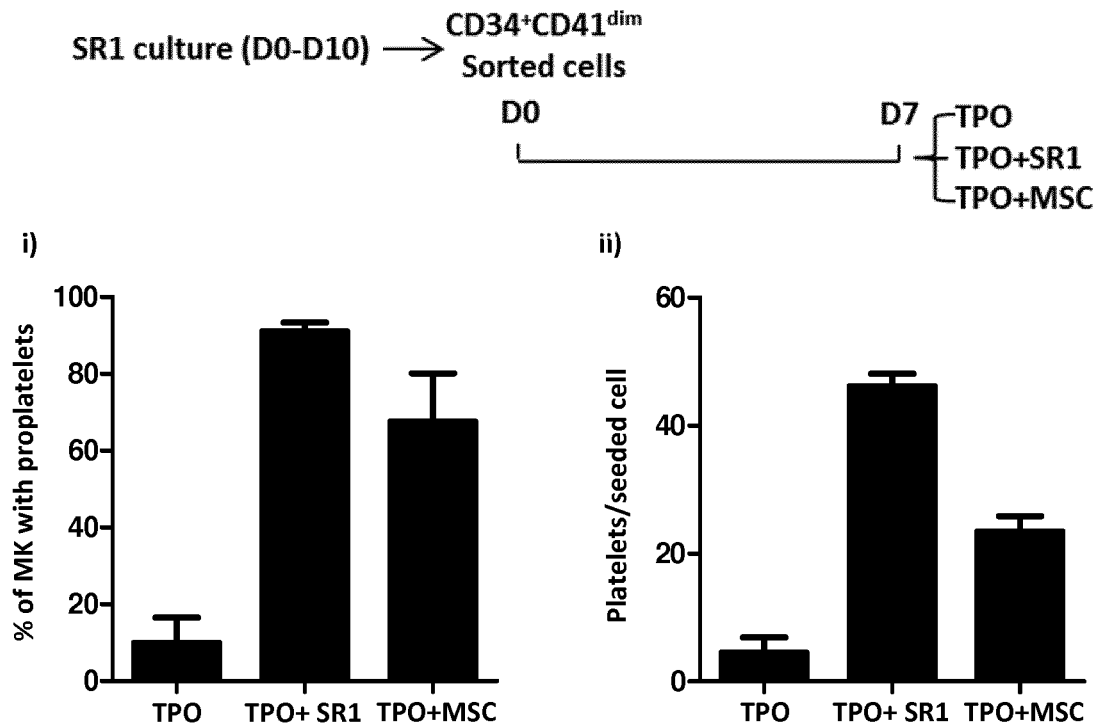
FIG. 9

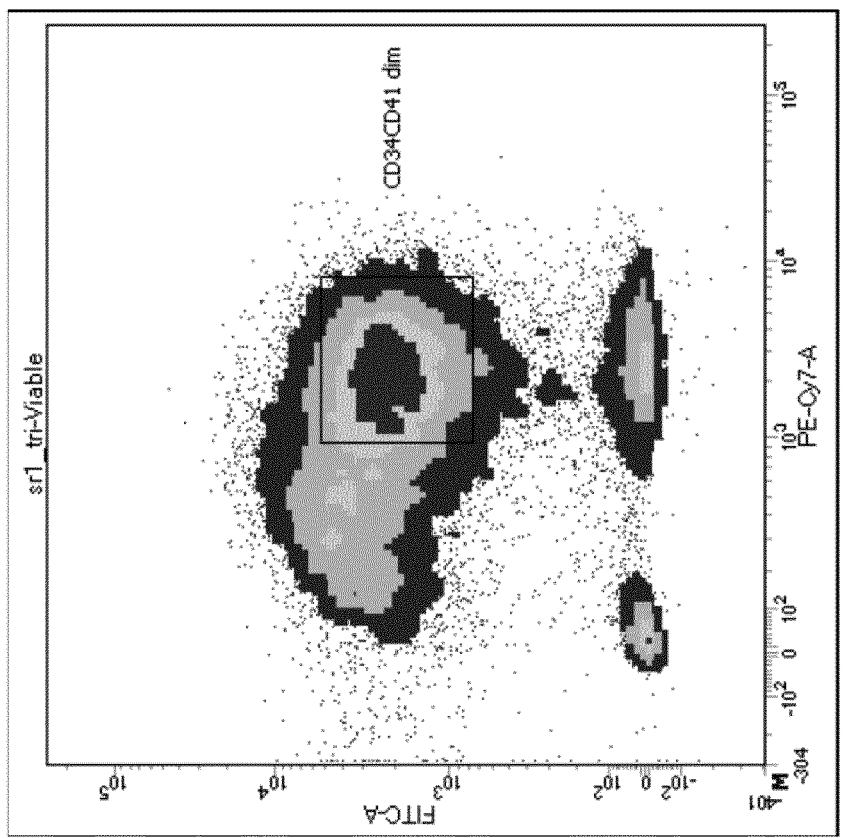
SR1 fluorescence intensity: 2546
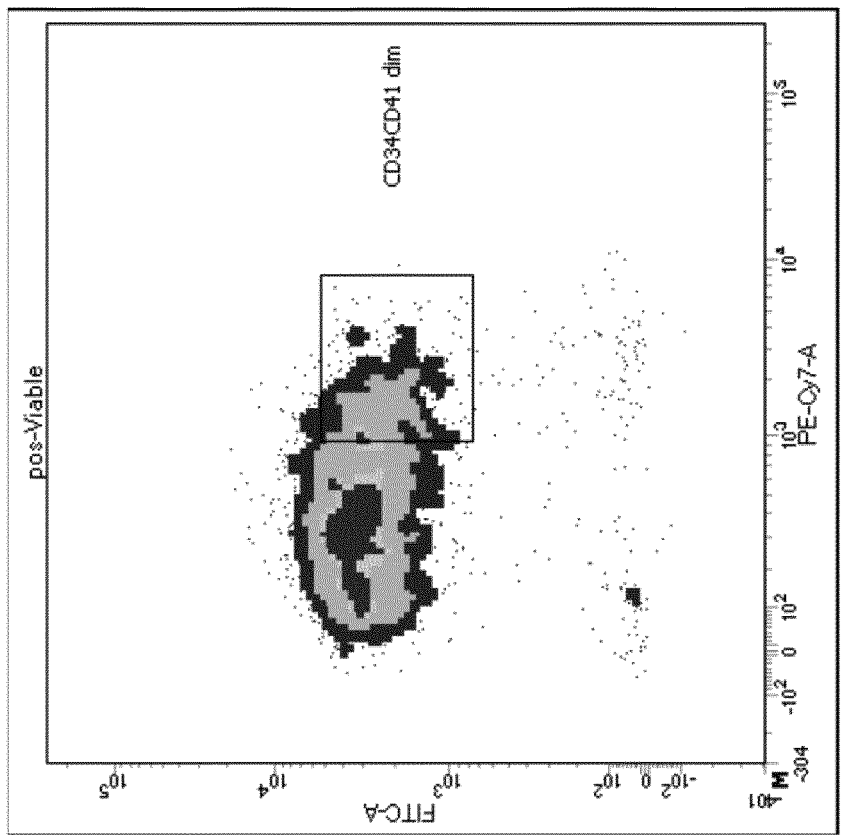
Control fluorescence intensity: 2734
FIG. 10

CD34+CD41$^{DIM}$ MEGAKARYOCYTES PROGENITORS AND USES THEREOF FOR PRODUCING PROPLATELET-BEARING MKS AND/OR PLATELETS

The invention relates to a method of producing CD34+CD41$^{dim}$ megakaryocyte (MK) progenitor cells, and substantially pure cell population of megakaryocyte precursor cells obtained by said method. The invention also relates to a method of producing proplatelet-bearing MKs and/or platelets using the CD34+CD41$^{dim}$ cells.

BACKGROUND

Blood platelets play crucial roles in both physiology and pathology and it is therefore of major importance to understand the mechanisms controlling their production. In adults, platelets are produced by bone marrow megakaryocytes (MKs) which themselves originate from hematopoietic stem and progenitor cells. In vitro production of platelets for transfusion has been the subject of many studies in recent years. Continuous improvements in the culture conditions make this an attainable goal, like the recent generation of transfusable human red cells. Nevertheless, we are still unable to efficiently reproduce the native process which can generate over 1000 platelets per MK (Reems J A et al., Transfusion medicine reviews. 2010; 24:33-43).

One way to improve in vitro platelet production would be to isolate and amplify MK progenitors with an increased capacity to mature to the proplatelet stage. In the accepted hierarchical map of hematopoiesis, MKs diverge from a common bipotent MK/erythroid progenitor (MEP) (Chen L et al., Science. 2014; 345:1251033). Although the existence of a separate MK progenitor has been suggested, no such univocal progenitor has yet been clearly identified or expanded from human adult hematopoietic cells. Rare human populations have been observed which appear to have an increased capacity to produce proplatelet-bearing MKs, but these cells have not been amplified or evaluated for in vitro platelet production (Debili N. et al., Blood. 1992; 80:3022-3035; Dercksen M W et al., Blood. 1995; 85:3313-3319; Norol F. et al., Blood. 1998; 91:830-843). In particular, CD41 positive cells have been described among human CD34+ cells isolated directly from bone marrow or after culture under MK promoting conditions (Debili N. et al., Blood. 1992; 80:3022-3035; Dercksen M W et al., Blood. 1995; 86:3771-3782). However, these populations were highly polyploid and unable to proliferate (Dercksen M W et al., Blood. 1995; 86:3771-3782). CD34+CD41+ cells have also been observed after co-culture of bone marrow-derived CD34+ cells on hMSCs without TPO, but no evidence was provided for a distinct CD41$^{dim}$ subpopulation (Cheng L. et al., Journal of cellular physiology. 2000; 184:58-69). Cells with a CD34+CD41$^{low}$ phenotype representing a very minor population were recently reported in cultures derived from peripheral blood but were not characterized further (Debili et al., Blood, 2001, 97(7), 2023-2030.

Classically, human MKs are differentiated in culture from CD34+ cells, a population containing hematopoietic stem cells and a mixture of progenitor cells with various potentials. Since the availability of TPO, numerous protocols have been devised to refine MK differentiation, using stepwise combinations of cytokines and growth factors with or without stromal cells (Sullenbarger B. et al., Experimental hematology. 2009; 37:101-110; Panuganti S. et al. Tissue engineering Part A. 2013; 19:998-1014; Pineault N. et al., Cytotherapy. 2011; 13:467-480). As a result, improvements have been reported in the ability to expand the number of input CD34+ cells and to differentiate MKs, as evidenced by their increased size and ploidy, the appearance of platelet-specific markers (CD41 and CD42) and their capacity to produce proplatelets. Despite this progress, the percentage of MKs reaching the proplatelet stage remains low and platelet production is well below that of MKs differentiated in situ in the bone marrow.

Transcriptomic databases have revealed that the aryl hydrocarbon receptor (AhR) is well expressed all along the pathway leading to MKs (HSC, CMP, MEP and MK) (Smith B W et al., Blood. 2013; 122:376-385). StemRegenin 1 (SR1), a recently developed high affinity AhR antagonist, was further reported to promote the expansion of hematopoietic progenitor cells (HPCs) (Boitano A E et al., Science. 2010; 329:1345-1348).

Methods for in vitro producing MK or platelets from hematopoietic stem cells, including a step of contacting with AhR modulators, have been disclosed.

WO 2012/129109 discloses an ex vivo three-step method for producing platelets which comprises a first step of generating megakaryocyte progenitor cell population by culturing stem cells in the presence of a plurality of growth factors selected from a group of 29 growth factors or families of growth factors, including SR1 and co-culture with mesenchymal stem cells. The method further comprises maturing the expanded megakaryocyte progenitor cells under conditions of increased oxygen concentration and in the presence of a plurality of growth factors, and culturing the matured megakaryocytes in a three-dimensional matrix, under conditions of increased oxygen concentration and in the presence of a plurality of growth factors, to produce platelets.

WO 2014/028749 discloses a method of making a megakaryocyte-erythroid progenitor cell (MEP), comprising differentiating a MEP precursor cells into a MEP in culture in the presence of an AhR modulator. The method comprises in particular culturing MEP precursor cells in the presence of an AhR antagonist and then culturing MEP precursor cells in the presence of an AhR agonist.

WO 2014/138485 discloses an ex vivo two-step method which comprises a first step of generating megakaryocytes by directed differentiation of hematopoietic stem cells and progenitor cell (HSPC) using platelet-derived growth factor receptor (PDGFR) antagonist and a combination of cytokines TPO, IL-6, Flt3-L and SCF, and a second step which promotes platelet biogenesis from the megakaryocytes using an AhR antagonist and TPO, IL-6, Flt3-L and SCF, or an AhR antagonist and TPO, and optionally further a matrix metalloproteinase (MMP) inhibitor.

SUMMARY OF THE INVENTION

The invention relates to an ex vivo method of producing proplatelet-bearing megakaryocytes (MKs) and/or platelets comprising:
a) Culturing an isolated CD34+CD41$^{dim}$ cell population of MK progenitors in a serum-free culture medium comprising thrombopoietin (TPO), in presence of an aryl hydrocarbon receptor (AhR) antagonist or by co-culture with human mesenchymal stromal cells (hMSCs), for a time sufficient to obtain a cell population comprising proplatelet-bearing MKs and/or platelets; and
b) Collecting said cell population comprising proplatelet-bearing MKs and/or platelets.

The invention further provides for a method of producing megakaryocyte (MK) progenitor cells comprising:

a0) Culturing haematopoietic stem cells (HSC) in a serum-free culture medium comprising low-density lipoprotein (LDL), stem cell factor (SCF), TPO, IL-6 and IL-9, in presence of an aryl hydrocarbon receptor (AhR) antagonist or by co-culture with human mesenchymal stromal cells (hMSCs), for a time sufficient to obtain a cell population comprising $CD34^+CD41^{dim}$ cells; and a1) isolating said $CD34^+CD41^{dim}$ cells from said cell population.

In another aspect the invention relates to a substantially pure cell population of megakaryocyte (MK) progenitors wherein at least 80% of the cells in the population are $CD34^+CD41^{dim}$ cells.

Also provided is a composition comprising a cell population of proplatelet-bearing megakaryocytes (MKs) and/or platelets and an infusion buffer for use for transfusion, wherein said use comprises preparing proplatelet-bearing megakaryocytes (MKs) and/or platelets by a method according to the invention.

DETAILED DISCLOSURE OF THE INVENTION

The inventors have found that SR1, a AhR antagonist, significantly improved the production of proplatelet-bearing MKs and platelet-like elements in two-step culture of peripheral blood haematopoietic stem cells (HSC). More importantly, culture with SR1 resulted in an enrichment of a $CD34^+CD41^{dim}$ population, which upon cell sorting exhibited an unprecedented capacity to mature to the proplatelet stage.

A similar enrichment of $CD34^+CD41^{dim}$ cells displaying a similar megakaryocytic potential was observed in HSC co-cultured with human mesenchymal stem cells (hMSCs). Co-culture with hMSCs, like SR1 treatment, led to repression of the AhR.

Moreover, the effects of SR1 and hMSCs were both prevented by an AhR agonist, indicating that the amplification of $CD34^+CD41^{dim}$ megakaryocytic precursors proceeds through repression of the AhR pathway.

Production of Megakaryocyte (MK) Progenitor Cells

The invention provides for a method of producing megakaryocyte (MK) progenitor cells comprising:

a0) Culturing haematopoietic stem cells (HSC) in a serum-free culture medium comprising low-density lipoprotein (LDL), stem cell factor (SCF), TPO, IL-6 and IL-9, in presence of an aryl hydrocarbon receptor (AhR) antagonist or by co-culture with human mesenchymal stromal cells (hMSCs), for a time sufficient to obtain a cell population comprising $CD34^+CD41^{dim}$ cells; and a1) isolating said $CD34^+CD41^{dim}$ cells from said cell population.

"Hematopoietic stem cells" (HSCs) as used herein refer to immature blood cells having the capacity to self-renew and to differentiate into more mature blood cells comprising granulocytes, erythrocytes, platelets, and monocytes. HSCs are interchangeably described as stem cells throughout the specification. In an embodiment HSC are CD34+ cells. CD34+ cells are believed to include a subpopulation of cells with the stem cell properties defined above. It is well known in the art that HSCs include pluripotent stem cells, multipotent stem cells (e.g., a lymphoid stem cell), and/or stem cells committed to specific hematopoietic lineages. Sources for HSC include unfractionated bone marrow, umbilical cord, and peripheral blood. For instance normal peripheral blood cells can be mobilized with G-CSF [leukapheresis (LK) cells], and CD34+ cells are isolated from LK cells by cell selection. HSC also include induced-pluripotent stem (iPS) cells committed to the hematopoietic lineage. iPS cells are well-known to one of skill in the art. By way of example, iPS cells can be obtained following the teachings of Takahashi & Yamanaka (2006) Cell 126:663-676 and Yamanaka et al. (2007) Nature 448:313-317. Preferably, the HSC are human cells.

The starting HSC population may preferably contain at least 60% CD34+ cells, in some embodiments, more than 80% of CD34+ cells, or even more than 90% of CD34+ cells. The starting HSC population may comprise between $10^5$ and $10^9$ nucleated cells For culturing, HSC are typically seeded at a cell density of $1\text{-}10\times10^4$ per mL of culture medium, for instance $2\text{-}6\times10^4$ per mL.

As used throughout the instant application, a "culture medium" denotes a "basal medium" which is supplemented with a mixture of cytokines, growth factors, and AhR antagonist which is specified at each step of the method. Preferably the basal medium is not supplemented with, i.e. the culture medium does not comprise, any additional component beside the mixtures of cytokines, growth factors, and AhR antagonist which is specified at each step. Preferably human cytokines and growth factors are used in the frame of the invention.

A "basal medium" is a synthetic serum free medium which typically comprises amino acids, carbon sources, vitamins, serum proteins (e.g. albumin), inorganic salts, divalent cations, buffers and any other element suitable for use in culturing of cells, and HSC in particular. The basal medium may typically contain or be supplemented with antibiotics to prevent contamination during cell culture, and glutamine. Growth factors and cytokines are typically not present into a basal medium.

Examples of such basal medium appropriate for a method of culturing HSC include, without limitation, StemSpan™ Serum-Free Expansion Medium (SFEM) (StemCell Technologies, Vancouver, Canada), StemSpan® H3000-Defined Medium (StemCell Technologies, Vancouver, Canada), CellGro® SCGM.

StemSpan™ Serum-Free Expansion Medium (SFEM) has been developed for the in vitro culture and expansion of human hematopoietic cells. This medium contains pre-tested bovine serum albumin, insulin and transferrin, and supplements in Iscove's MDM. Recombinant hematopoietic growth factors, required for the optimal growth and expansion of hematopoietic cells, are not present into StemSpan™ SFEM.

For the production of MK progenitor cells, the basal medium is supplemented with low-density lipoprotein (LDL), stem cell factor (SCF), TPO, IL-6 and IL-9.

In an embodiment the culture medium comprises SCF, TPO, IL-6 and IL-9 each present in a concentration of 1-100 ng/mL, such as 25-100 ng/mL, in particular 10-50 ng/mL, 40-50 ng/mL, or 20-30 ng/mL.

The basal medium is preferably supplemented with LDL 1-40 μg/mL for instance 10-30 μg/mL, or 15-25 μg/mL.

In particular, the culture medium may comprise 10-30 μg/mL LDL, 25-100 ng/mL SCF, 40-50 ng/mL TPO, 20-30 ng/mL IL-6, and 20-30 ng/mL IL-9.

In an embodiment, SCF, TPO, IL-6 and IL-9 are added to the basal medium by addition of the StemSpan™ Megakaryocyte Expansion Supplement (formerly known as CC220) (StemCell Technologies, Vancouver, Canada). StemSpan™ Megakaryocyte Expansion Supplement is supplied as a 100× concentrate and it contains a combination of recombinant human cytokines (SCF, IL-6, IL-9 and TPO) formulated to selectively promote the expansion and differentiation of human megakaryocyte progenitor cells in liquid cultures initiated with CD34+ cord blood (CB) or bone marrow (BM) cells.

The culture of HSC for producing a cell population comprising CD34$^+$CD41$^{dim}$ cells is further conducted in presence of an aryl hydrocarbon receptor (AhR) antagonist or by co-culture with human mesenchymal stromal cells (hMSCs).

In an embodiment, the AhR antagonist is a synthetic compound added to the basal medium which has formula (I)

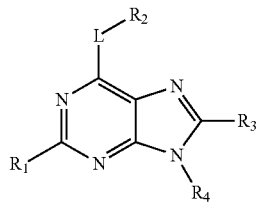

or a pharmaceutically acceptable salt, or stereoisomer thereof; wherein

L is selected from —NR$_{5a}$(CH$_2$)$_{2-3}$-, —NR$_{5a}$(CH$_2$)$_2$NR$_{5b}$—, —NR$_{5a}$(CH$_2$)$_2$S—, —NR$_{5a}$CH$_2$CH(OH)— and —NR$_{5a}$CH(CH$_3$)CH$_2$—; wherein R$_{5a}$ and R$_{5b}$ are independently selected from hydrogen and C$_{1-4}$alkyl;

R$_1$ is selected thiophenyl, furanyl, benzoimidazolyl, isoquinolinyl, imidazopyridinyl, benzothiophenyl, pyrimidinyl, pyrazolyl, pyridinyl, imidazolyl, pyrrolidinyl, pyrazinyl, pyridazinyl, pyrrolyl and thiazolyl; wherein said thiophenyl, furanyl, benzoimidazolyl, isoquinolinyl, imidazopyridinyl, benzothiophenyl, pyrimidinyl, pyrazolyl, pyridinyl, imidazolyl, pyrrolidinyl, pyrazinyl, pyridazinyl, pyrrolyl and thiazolyl of R$_1$ is optionally substituted by 1 to 3 radicals independently selected from halo, cyano, C$_{1-4}$alkyl, halo-substituted-C$_{1-4}$alkyl, C$_{1-4}$alkoxy, —S(O)$_{0-2}$R$_{8a}$, and —C(O)OR$_{8a}$, wherein R$_{8a}$ is selected from hydrogen and C$_{1-4}$alkyl;

R$_2$ is selected from —S(O)$_2$NR$_{6a}$R$_{6b}$, —NR$_{6a}$C(O)NR$_{6b}$R$_{6c}$, phenyl, pyrrolopyridinyl, indolyl, thiophenyl, pyridinyl, triazolyl, 2-oxoimidazolidinyl, pyrazolyl, and indazolyl; wherein R$_{6a}$, R$_{6b}$ and R$_{6c}$ are independently selected from hydrogen and C$_{1-4}$alkyl;

and said phenyl, pyrrolopyridinyl, indolyl, thiophenyl, pyridinyl, triazolyl, oxoimidazolidinyl, pyrazolyl, or indazolyl of R$_2$ is optionally substituted with 1 to 3 radicals independently selected from hydroxy, halo, methyl, methoxy, amino, —O(CH$_2$)$_n$NR$_{7a}$R$_{7b}$, —OS(O)$_2$NR$_{7a}$R$_{7b}$ and —NR$_{7a}$S(O)$_2$R$_{7b}$; wherein R$_{7a}$ and R$_{7b}$ are independently selected from hydrogen and C$_{1-4}$alkyl;

R$_3$ is selected from hydrogen, C$_{1-4}$alkyl and biphenyl; and

R$_4$ is selected from C$_{1-10}$alkyl, C$_{1-4}$alkenyl, oxetanyl, tetrahydrofuranyl, cyclohexyl, (oxopyrrolidinyl)ethyl, tetrahydropyranyl, phenyl, and benzyl, wherein said C$_{1-10}$alkyl, C$_{1-4}$alkenyl, oxetanyl, tetrahydrofuranyl, cyclohexyl, (oxopyrrolidinyl)ethyl, tetrahydropyranyl, phenyl, and benzyl of R$_4$ can be optionally substituted with 1 to 3 radicals independently selected from hydroxy, C$_{1-4}$alkyl and halo-substituted-C$_{1-4}$alkyl.

In an embodiment, the AhR antagonist of formula (I) is StemRegenin 1 (SR1), i.e. 4-(2-(2-(benzo[b]thiophen-3-yl)-9-isopropyl-9H-purin-6-ylamino)ethyl)phenol.

During step a0), the AhR antagonist is typically present in the culture medium at a concentration of 10 nM to 10 µM, for instance 100 nM to 7.5 µM, in particular 1 to 5 µM.

In another embodiment, the HSC are co-cultured with human mesenchymal stromal cells (hMSCs) in the culture medium comprising LDL, SCF, TPO, IL-6 and IL-9. As shown by the inventors in the following example, the effect of co-culture with hMSCs is reversed by addition of the AhR agonist FICZ, and co-culture with hMSCs drastically decreases transcription of CYP1B1, a downstream target of AhR. These results thus substantiate that co-culture with hMSCs antagonizes the AhR pathway.

According to an embodiment, said hMSCs are obtained by a method comprising:
i) Isolating bone marrow mononuclear cells (BM-MNCs) from a healthy human subject by Ficoll density gradient;
ii) Seeding isolated BM-MNCs in culture medium comprising 5-15% fetal bovine serum and 0.5-5 ng/mL fibroblast growth factor 2 (FGF-2), for instance 1 ng/mL FGF-2;
iii) Culturing seeded cells for two days, and the discarding nonadherent cells and seeding collected adherent cells;
iv) Culturing adherent cells in culture medium comprising 10% fetal bovine serum and 0.5-5 ng/mL FGF-2 (for instance 4 ng/mL), with replacement of culture medium twice a week with fresh culture medium until confluence; and
v) Harvesting hMSCs, seeding and culturing harvested cells until confluence in culture medium comprising 10% fetal bovine serum and 0.5-5 ng/mL FGF-2.

At step ii), BM-MNCs are seeded for instance at a cell density of 10$^4$ cells/cm$^2$.

Harvesting hMSCs is typically performed using trypsin. Cells are then typically seeded at a cell density of 500 cells/cm$^2$ and cultured until confluence (first passage, P1). hMSCs display a lack of CD45, CD14, CD34, and CD31 expression, together with a strong expression of CD73, CD90, and CD105.

hMSCs can be maintained in culture medium comprising 10% fetal bovine serum and 0.5-5 ng/mL FGF-2, for instance 2 ng/mL FGF2.

hMSCs are used in a confluent layer and CD34$^+$ cells are typically added at the above specified cell density.

The culture medium used for producing and maintaining the hMSCs is any culture medium suitable for the culture of mesenchymal cells, such as α-MEM.

For producing MK progenitor cells, in step a0), culturing of HSC is conducted for 6 to 8 days, preferably 7 days.

The cultures are typically incubated at 37° C., under normoxic conditions (i.e. 20-21% O$_2$), and 5% CO$_2$.

At the end of the culture period, the culture comprises CD34$^+$CD41$^{dim}$ cells which are isolated from the cell culture by any suitable method known to the skilled person.

Typically, cells in suspension are harvested and washed with a suitable buffer such as PBS.

Methods for isolating the CD34$^+$CD41$^{dim}$ cell population based on CD34 and CD41 markers uses flow cytometry, more specifically fluorescent activated cell sorting (FACS) technology. To that end, cells in suspension harvested from the cell culture are incubated with a mixture of labeled anti-CD34 and anti-CD41 antibodies. Incubation can be typically performed for 20-40 minutes at 4° C. Cells are then washed before cell sorting by FACS.

Only viable CD34$^+$CD41$^{dim}$ cells are selected from the harvested cell population. According to this embodiment washed cells are further incubated with a fluorescent marker of cell viability, such as 7-aminoactinomycine D (7-AAD) or Hoechst which are a marker of DNA. Incubation is performed typically for 20-40 minutes at 4° C. Cells are then washed before cell sorting by FACS.

The FACS morphologic and sorting gates are typically positioned as follows:
CD34: from $10^{0.2}$ to $10^{1.2}$;
CD41: from log $10^1$ to log $10^2$.

The CD34$^+$CD41$^{dim}$ cell population can be readily identified as culture in presence of AhR antagonist, such as SR1, gives rise to a CD34+CD41+ cell population displaying a mean fluorescence intensity lower compared to control condition and which may be identified as shown on FIG. 10.

The CD34$^+$CD41$^{dim}$ cells selected are characterized by any one of the following features, or the combination thereof:
a small size, typically FSC: 200-400, SSC: 200;
low ploidy, typically 2n–4n;
a high capacity to mature into pure MKs, typically one CD34$^+$CD41$^{dim}$ cell can generate 2-3 MKs.

The method described therein produces at least 150,000 CD34$^+$CD41$^{dim}$ cells per seeded HSC, in particular CD34+ cell.

The invention further relates to a substantially pure cell population of MK progenitors, wherein at least 80%, preferably, at least 85%, 90%, 95%, of the cells in the population are CD34$^+$CD41$^{dim}$ cells.

In an embodiment, said substantially pure cell population of MK progenitors comprises at least 150,000 CD34$^+$CD41$^{dim}$ cells.

Said substantially pure cell population of MK progenitors is obtainable, or obtained, by the method of producing megakaryocyte (MK) progenitor cells.

The inventors further isolated a subpopulation of CD34$^+$CD41$^{dim}$ cells using CD9 sorting, which subpopulation is called CD34$^+$CD9$^-$CD41$^+$. This subpopulation CD34$^+$CD9$^-$CD41 was obtained from peripheral blood CD34$^+$ cells cultured in the presence of SR1 for 10 days from which CD34$^+$CD9$^-$ progenitors cells were gated by cell sorting. The population of CD34$^+$CD9$^-$ progenitor cells was then fractionated into MK progenitors according to the FSC/CD41$^+$ expression as further explained in example 2. The resulting subpopulation was thus identified as a CD34$^+$CD9$^-$CD41 cell population.

Figure 11:
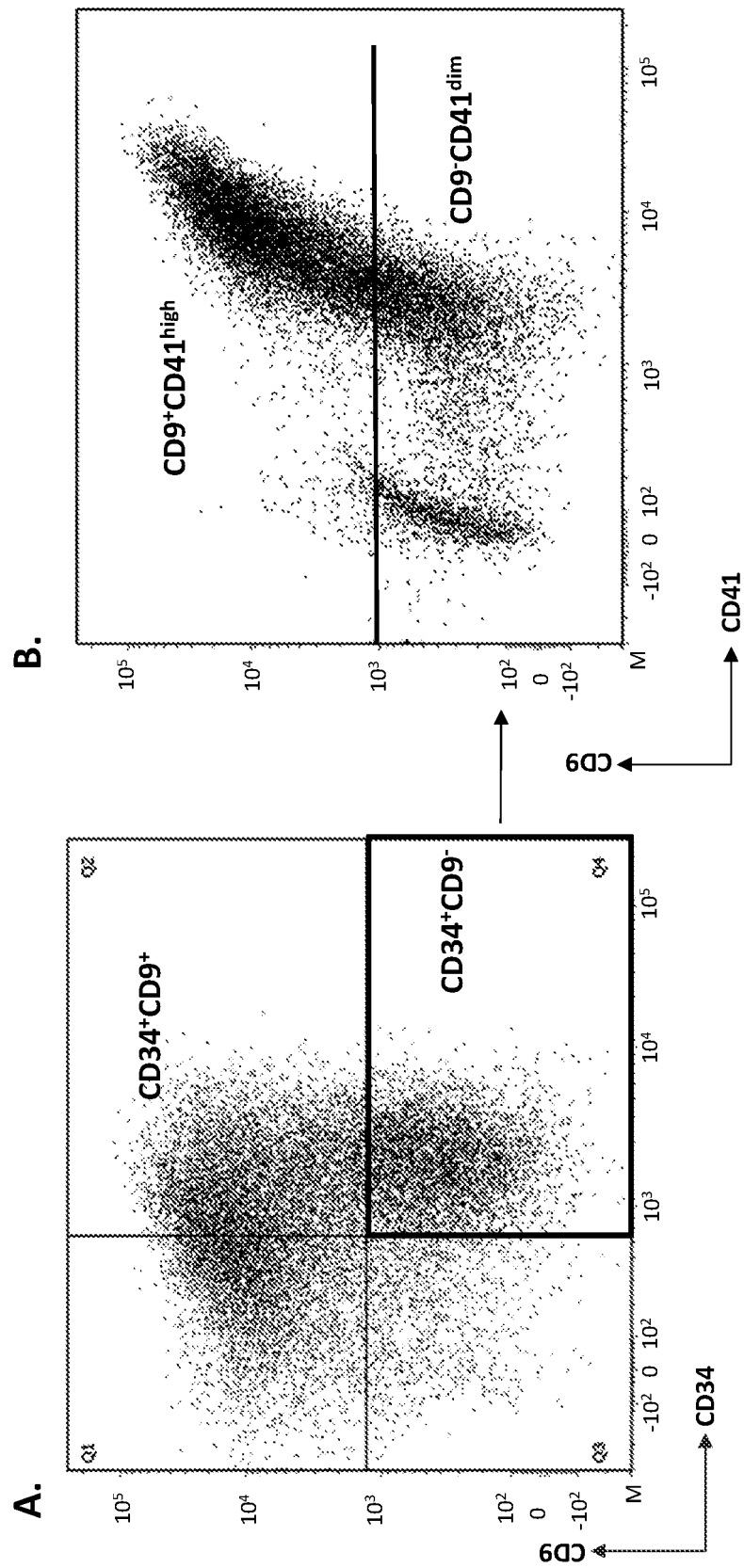

It will be understood by the skilled in the art, in particular in view of FIG. 11, that gating CD9$^-$ cells excludes CD41$^{high}$ cells. Accordingly, the remaining CD41$^+$ cells as gated by FSC/CD41$^+$ expression are CD41$^{dim}$ cells. It will be thus further understood by the skilled in the art that the CD34$^+$CD9$^-$CD41$^+$ cell population, as identified by the inventors, can also be called a CD34$^+$CD9$^-$CD41$^{dim}$ cell population.

Accordingly, in the following, the CD34$^+$CD9$^-$CD41$^+$ subpopulation can be indifferently referred to as CD34$^+$CD9$^-$CD41$^{dim}$.

The use of this subpopulation of CD34$^+$CD9$^-$CD41$^{dim}$ cells allows to further increase by 1.8 fold the platelet release compared to the use of CD34$^+$CD41$^{dim}$ cells.

According to the above, in one embodiment, in step a0) of the method of producing megakaryocyte (MK) progenitor cells the cell population comprising CD34$^+$CD41$^{dim}$ cells is a cell population comprising CD34$^+$CD9$^-$CD41$^{dim}$ and in step a1) said CD34$^+$CD9$^-$CD41$^{dim}$ cell population is isolated.

Accordingly, in one embodiment, the invention refers to a method of producing megakaryocyte (MK) progenitor cells comprising:
a0) Culturing haematopoietic stem cells (HSC) in a serum-free culture medium comprising low-density lipoprotein (LDL), stem cell factor (SCF), TPO, IL-6 and IL-9, in presence of an aryl hydrocarbon receptor (AhR) antagonist or by co-culture with human mesenchymal stromal cells (hMSCs), for a time sufficient to obtain a cell population comprising CD34$^+$CD9$^-$CD41$^{dim}$; and
a1) isolating said CD34$^+$CD9$^-$CD41$^{dim}$ cells from said cell population.

Similar to CD34$^+$CD41$^{dim}$ cells CD34$^+$CD9$^-$CD41$^{dim}$ cells are characterized by any one of the following features, or the combination thereof:
a small size, typically FSC: 200-400, SSC: 200;
low ploidy, typically 2n–4n;
a high capacity to mature into pure MKs, typically one CD34+CD41dim cell can generate 2-3 MKs.

Methods for isolating the CD34$^+$CD9$^-$CD41$^{dim}$ cell population based on CD34 and CD41 markers uses flow cytometry, more specifically fluorescent activated cell sorting (FACS) technology. To that end, cells in suspension harvested from the cell culture are incubated with a mixture of labeled anti-CD34 and anti-CD9 antibodies. Incubation can be typically performed for 20-40 minutes at 4° C. Cells are then washed before cell sorting by FACS.

Only viable CD34$^+$CD9$^-$ cells are selected from the harvested cell population. According to this embodiment washed cells are further incubated with a fluorescent marker of cell viability, such as 7-aminoactinomycine D (7-AAD) or Hoechst which are a marker of DNA. Incubation is performed typically for 20-40 minutes at 4° C. Cells are then washed before cell sorting by FACS. Using the CD9$^-$ cell surface marker for sorting excludes CD41 high cells. The resulting viable CD34$^+$CD9$^-$ are then further sorted into MK progenitors according to the FSC/CD41$^+$ expression allowing obtaining a population of CD34$^+$CD9$^-$CD41$^{dim}$ cells.

In one embodiment, the CD34$^+$CD9$^-$CD41$^{dim}$ cell population represents 40 to 80% of the CD34$^+$CD41$^{dim}$ cell population, preferably 45 to 75%, such as 50 to 70%, 55 to 65%, more preferably 60%.

The invention further relates to a substantially pure cell population of MK progenitors, wherein at least 50%, preferably, at least 55%, 60%, more preferably 80% such as 85%, 90%, 95%, of the cells in the population are CD34$^+$CD9$^-$CD41$^{dim}$ cells.

In an embodiment, said substantially pure cell population of MK progenitors comprises at least 150,000 CD34$^+$CD9$^-$CD41$^{dim}$ cells.

Said substantially pure cell population of MK progenitors is obtainable, or obtained, by the method of producing megakaryocyte (MK) progenitor cells.

Production of Proplatelet-Bearing Megakaryocytes (MKs) and/or Platelets

The invention further provides for a method of producing proplatelet-bearing megakaryocytes (MKs) and/or platelets comprising:
a) Culturing said isolated CD34$^+$CD41$^{dim}$ cell population of MK progenitors in a serum-free culture medium comprising thrombopoietin (TPO), in presence of an aryl hydrocarbon receptor (AhR) antagonist or by co-culture with human mesenchymal stromal cells (hMSCs), for a time sufficient to obtain a cell population comprising proplatelet-bearing MKs and/or platelets; and b) Collecting said cell population comprising proplatelet-bearing MKs and/or platelets.

For culturing, CD34+CD41$^{dim}$ cells are typically seeded at a cell density of 1-10×10$^4$ per mL of serum-free culture medium, for instance 2-6×10$^4$ per mL.

For the production of proplatelet-bearing MKs and/or platelets, the basal medium is supplemented with TPO and the culture is conducted in presence of AhR antagonist.

The term "serum-free culture medium", "basal medium" and "aryl hydrocarbon receptor (AhR) antagonist" are as defined previously.

In an embodiment, the culture medium comprises 20-100 ng/ml TPO, preferably 25-65 ng/ml, still preferably 40-60 ng/ml.

In step a), an AhR antagonist, in particular a compound of formula (I)

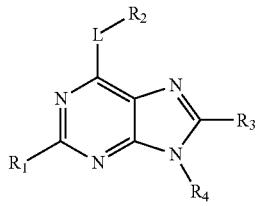

as defined above,
or a co-culture with hMSCs is used independently from the AhR antagonist or co-culture with hMSCs used in step a0) for producing CD34+CD41$^{dim}$ cells.

Therefore altogether, the following embodiments are encompassed by the invention:
  in both steps a0) and a) an AhR antagonist is used, in particular a compound of formula (I), or a co-culture with hMSCs is performed;
  in step a0), an AhR antagonist, in particular a compound of formula (I), is used, while in step a) a co-culture with hMSCs is performed; and
  in step a0), a co-culture with hMSCs is performed, and in step a), an AhR antagonist, and in particular a compound of formula (I), is used.

The cultures are typically incubated at 37° C., under normoxic conditions (i.e. 20-21% $O_2$), and 5% $CO_2$.

In an embodiment, the step a) of culturing is conducted for 5 to 9 days, preferably for 6-8 days, still preferably for about 7 days.

At the end of the culture period, cells in suspension are harvested from the culture, thereby collecting proplatelet-bearing MKs and/or platelets present in the cell culture.

Proplatelet-bearing MKs can be identified by phase-contrast microscopy by detecting round and pro-platelet bearing cells.

In one embodiment, the CD34+CD41$^{dim}$ cell population of MK progenitors is a CD34+CD9−CD41$^{dim}$ cell population of MK progenitors.

Accordingly, in one embodiment, the invention relates to an ex vivo method of producing proplatelet-bearing megakaryocytes (MKs) and/or platelets comprising:
  a) Culturing an isolated CD34+CD9−CD41$^{dim}$ cell population of MK progenitors in a serum-free culture medium comprising thrombopoietin (TPO), in presence of an aryl hydrocarbon receptor (AhR) antagonist or by co-culture with human mesenchymal stromal cells (hMSCs), for a time sufficient to obtain a cell population comprising proplatelet-bearing MKs and/or platelets; and b) Collecting said cell population comprising proplatelet-bearing MKs and/or platelets.

In an embodiment, the method further comprises selecting CD41/CD61+ and CD42c+ cells from the collected cell population comprising proplatelet-bearing MKs and/or platelets. Platelets or platelet-like particles are identified as CD41 and CD42c double positive events, having the same scattering properties as human blood platelets.

After cell sorting based on CD41 and CD42c markers, the cell population comprising proplatelet-bearing MKs and/or platelets typically comprises at least 75%, preferably 80%, 85%; 90%, 92% or 95% proplatelet-bearing MKs and/or platelets.

Preferably, the cell population comprising proplatelet-bearing MKs and/or platelets comprises at least 50,000 CD41+CD42c+ cells, obtained from 20,000 CD34+CD41$^{dim}$ seeded cells. About 90% of the MKs produced using an AhR antagonist such as SR1, and about 50% of the MKs produced using a co-culture with hMSC are proplatelet-bearing MKs.

The method described herein thus produces at least 2, preferably at least 2.5, such as 2.7 proplatelet-bearing MKs per seeded CD34+CD41$^{dim}$ cell. About 1.10$^6$ platelets are obtained from 20,000 CD34+CD41$^{dim}$ seeded cells, hence about 50 platelets per CD34+CD41$^{dim}$ seeded cell.

In one embodiment, the method described herein produces at least 3.6, preferably at least 4.5, such as 4.8 MKs per seeded CD34+CD9−CD41$^{dim}$ cell. About 1.8×10$^6$ platelets are obtained from 20,000 CD34+CD9−CD41$^{dim}$ seeded cells, hence about 90 platelets per CD34+CD9−CD41$^{dim}$ seeded cell.

The method of producing proplatelet-bearing MKs and/or platelets can further comprise washing the collected proplatelet-bearing MKs and/or platelets and suspending the washed cells in an infusion buffer.

This may be readily achieved by pelleting the cells by centrifugation, for instance for 10 minutes at 1000 g, and resuspending the cells in infusion buffer e.g., a 5% HSA (Baxter) at a concentration of between 10$^7$ to 10$^{10}$ proplatelet-bearing MKs and/or platelets/ml.

The method of the invention can produce platelets in a patient specific manner by using HLA-matched CD34+ cells.

Compositions and Therapeutic Treatments

The invention further relates to a composition comprising a cell population of proplatelet-bearing megakaryocytes (MKs) and/or platelets, in particular CD41 and CD42c+ cells, and an infusion buffer obtainable or obtained by the method of the invention.

The invention also relates to said composition for its use for allogeneic or autologous transfusion. In an embodiment, in the composition for use for transfusion, said use comprises preparing proplatelet-bearing megakaryocytes (MKs) and/or platelets by a method according to the invention.

It is further provided a method of transfusion of a patient in need thereof, which comprises:
  a) preparing a composition comprising a cell population of proplatelet-bearing megakaryocytes (MKs) and/or platelets and an infusion buffer by the method of the invention;
  b) transfusing said composition to a patient in need thereof.

The subject according to the invention is a mammal, such as a rodent, a canine, a feline or a primate. Preferably the subject is a human.

The number of cells transfused typically takes into consideration factors such as sex, age, weight, the types of disease or disorder, stage of the disorder, the percentage of the desired cells in the cell population and the amount of cells needed to produce a therapeutic benefit. In one particular embodiment, the composition is administered by intravenous infusion and comprises at least $10^8$ platelets/kg, from $10^9$ to $10^{10}$ platelets/kg or more if needed. A transfusion dose is typical about 3 to $5\times10^{11}$ platelets.

The invention will be further illustrated in view of the following figures and examples.

FIGURES

FIG. 1: Preservation of CD34 expression in MKs cultured in the presence of SR1. (A) MK differentiation protocol. Peripheral blood CD34+ cells were cultured in the absence (Ctrl) or presence of SR1 (1 µM) in a serum-free medium containing CC220 cytokine cocktail from day 0 to day 7 and with TPO (30 ng/mL) from day 7 to day 14. (B) Level of proliferation. Viable cells were counted on days 7 and 10 of culture using an automatic cell counter and the fold increase over the input of CD34+ cells on day 0 was calculated. (C) Proportion of CD34+ cells. The proportion of CD34+ cells was determined on the indicated days by flow cytometry after labeling with an R-PE-Cy5-conjugated anti-CD34 mAb. Experiments were performed at least three times (mean±SEM; two-way ANOVA and a Bonferroni post-test, n.s. P>0.05, ***P<0.001).

FIG. 2: Increased production of proplatelets and platelet-like elements in the presence of SR1. CD34+ cells were cultured as in FIG. 1A and analyses were performed on day 14. (A) Quantification of the percentage of MKs extending proplatelets (34.6±2.1% with SR1 versus 11.5±4.5% for the control; mean±SEM in 3 experiments; Student's t-test *P<0.05). (B) Release of platelets. The cell suspension was subjected to multiple pipetting and platelet-like elements were detected and counted by flow cytometry. Upper panel: Representative gating strategy based on the forward and side scattering properties and CD41/CD42 expression of the cells. Lower panel: Number of platelet-like elements per cell seeded on day 7 (7.92±3.25 for the control vs 20.72±5.19 with 1 µM SR1 vs 0.20±0.04 with 0.2 µM of the AhR agonist FICZ) mean±SEM in 3 to 5 experiments; two-way ANOVA and a Bonferroni post-test, n.s. P>0.05).

FIG. 3: Emergence of a CD34+CD41$^{dim}$ population in the presence of SR1. CD34+ cells were cultured as in FIG. 1A and analyses were performed on days 7 and 10. (A) Evolution of CD34 and CD41 expression. Representative flow cytometric dot plots in the absence (Ctrl) or presence of SR1. On day 7, three main populations were observed which were CD34+CD41− (purple), CD34+CD41+ (red) and CD34−CD41+ (blue) and represented respectively 23.1±1.3%, 59.9±2.3% and 9.7±1.1% of the total population in the control versus 22.4±1.5%, 68.9±1.8% and 3.6±0.3% in the presence of SR1. On day 10, the two main populations were CD34−CD41+ and CD34+CD41+. CD34−CD41+ cells amounted to 51.6±4.9% of the cells in the control versus 26.7±4.5% in the presence of SR1. The CD34+CD41 population (red) was more abundant in SR1-treated cultures (55.1±4.9%) than under control conditions (32.1±0.7%). A CD34+CD41+ subpopulation (region R2) with an intermediate level of CD41 expression, defined as CD34+CD41$^{dim}$, was predominant in SR1 cultures. (B) Proportion of CD34+ CD41$^{dim}$ cells. Bar graph representing the percentage of CD34+CD41$^{dim}$ cells gated in R$_2$, which amounted to 16.8±1.4% of the total cells in the control versus 36.8±1.9% after SR1 treatment (mean±SEM in 8 experiments; Student's t-test, ***P<0.001). (C) Dot plots of forward light scattering versus CD41 expression showing the CD34+ CD41$^{dim}$ population (red) and the CD34−CD41+ population (blue) from an SR1-treated culture on day 10.

FIG. 4 Ploidy distribution of the CD34+CD41dim and CD34−CD41+ cells from an SR1-treated culture on day 10 (Student's t-test, *P<0.05, **P<0.005).

FIG. 5. High capacity of CD34+CD41$^{dim}$ cells to produce proplatelets and platelet-like elements. (A) CD34+ cells cultured for 10 days in the presence of SR1 as in FIG. 1A were sorted according to their CD34+CD41$^{dim}$ and CD34− CD41 expression using a FACS Aria II flow cytometer and then cultured for 7 days in a medium containing TPO with or without SR1 (5 µM). (B) Quantification of the percentage of MKs extending proplatelets 7 days after seeding CD34+ CD41$^{dim}$ cells (91.0±2.4% with SR1 versus 10.0±6.6% for the control; mean±SEM in 5 experiments; Student's t-test, *P<0.001). (C) Number of platelet-like elements 7 days after seeding CD34+CD41$^{dim}$ cells (52.1±8.8 with SR1 versus 7.7±0.8 for the control; mean±SEM in 5-8 experiments; Student's t-test, P<0.005).

FIG. 6. Co-culture of CD34+ cells with hMSCs promotes platelet production and the emergence of a CD34+CD41$^{dim}$ population. (A) CD34+ cells were cultured as in FIG. 1A in the absence (Ctrl) or presence of a monolayer of hMSCs for up to 14 days. (B) Level of proliferation. Viable cells were counted on days 7 and 10 of culture using an automatic cell counter and the fold increase over the input of CD34+ cells was calculated (mean±SEM in 3 experiments; Student's t-test, n.s. P>0.05). (C) Quantification of culture-derived platelets. The cell suspension was subjected to multiple pipetting on day 14 of culture and platelet-like elements were detected and counted by flow cytometry (mean±SEM in 3 experiments; Student's t-test, *P<0.05).

FIG. 7. (A) Effect of FICZ on platelet production. CD34+ cells were co-cultured on MSCs as in FIG. 5A in the presence or absence of the AhR agonist FICZ (0.2 µM). On day 14, platelet-like elements were counted by flow cytometry (20.6±1.3 vs 4.5±1.9 per cell seeded on day 7, with or without FICZ, respectively; mean±SEM in 3 experiments; Student's t-test, *** P<0.001? (B) CYP1B1 expression. qPCR analysis of CYP1B1 mRNA on day 10 in MKs co-cultured or not with MSCs or SR1 and with or without FICZ. Data are the mean values±SEM of 3 experiments.

Figure 8:
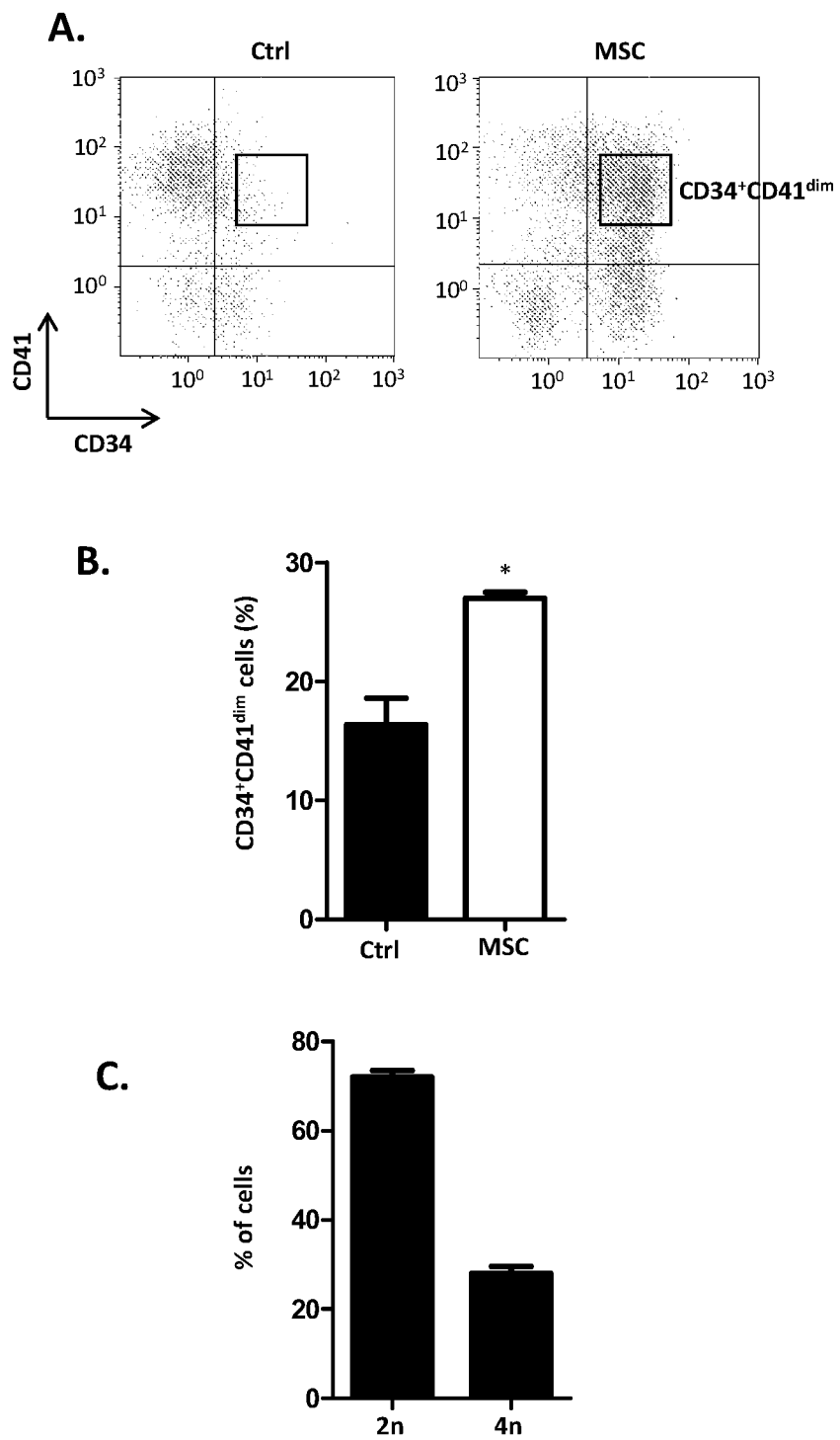

FIG. 8. (A) Evolution of CD34 and CD41 expression. Representative flow cytometric dot plots of CD34 and CD41 expression in the cell suspension on day 10 revealing a CD34+CD41$^{dim}$ population in MSC co-cultures. (B) Proportion of CD34+CD41$^{dim}$ cells. Bar graph representing the proportion of cells in the CD34+CD41$^{dim}$ region (mean±SEM in 3 experiments; Student's t-test, *P<0.05). (C) Ploidy distribution of the CD34+CD41$^{dim}$ cells from an MSC co-culture on day 10.

FIG. 9. Comparable properties of CD34+CD41$^{dim}$ cells obtained after treatment with MSCs or SR1. (A) CD34+ cells were cultured for 10 days as in FIG. 1A in the presence of a monolayer of MSCs. CD34+CD41$^{dim}$ cells were sorted on day 10 and cultured for a further 7 days with TPO, TPO+5 µM SR1, or TPO+MSC. Panel i: Quantification of the percentage of MKs extending proplatelets. Panel ii: Quantification of culture-derived platelets. (B) CD34+ cells were cultured for 10 days as in FIG. 1A in the presence of 5 µM SR1. CD34+CD41$^{dim}$ cells were sorted on day 10 and cultured for a further 7 days with TPO, TPO+5 µM SR1, or TPO+MSC. Panel i: Quantification of the percentage of MKs extending proplatelets. Panel ii: Quantification of culture-derived platelets. Mean±SEM in 3-4 experiments.

FIG. 10. Density plot allowing visualizing the cell population CD34+CD41$^{dim}$.

FIG. 11. Visualisation of the CD41 population among the CD9 population. A) Representative flow cytometric dot plot of CD34 and CD9 expression in the cell suspension on day 10. The region in the right lower inlet represents the CD34+CD9− cell population that is gated in Example 2. B) Representative flow cytometric dot plot of CD41 and CD9 expression in the cell suspension on day 10. The region in the right lower inlet of A) representing the CD34+CD9− cell population corresponds in the lower inlet of the CD41/CD9 dot plot which is CD9−CD41$^{dim}$. It can be concluded that the CD9− cell population is identical with the CD9−CD41$^{dim}$ cell population.

Figure 12:
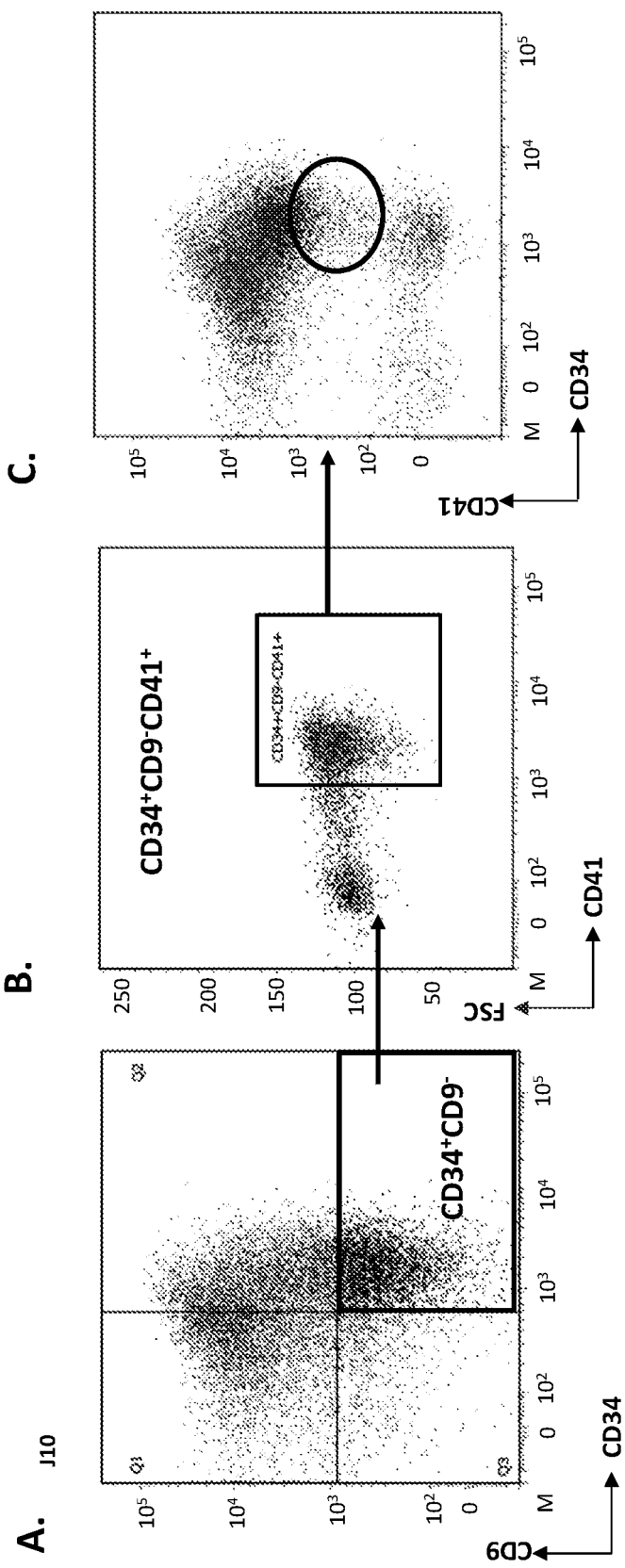

FIG. 12. Visualisation of the CD34+CD9−CD41$^{dim}$ cell population in comparison to the CD34+CD41$^{dim}$ cell population A) Representative flow cytometric dot plot of CD34 and CD9 expression in the cell suspension on day 10. The right lower inlet represents the CD34+CD9− cell population that is gated in Example 2. B) Representative flow cytometric dot plot of FSC/CD41+ expression of the CD34+CD9− cell population. The inlet in B) represents the CD34+CD9−CD41+ cell population. CD9− deselects CD41$_{high}$. The remaining CD41+ cells as gated by FSC/CD41+ expression are thus CD41$^{dim}$. The CD34+CD9−CD41+ cell population can be called a CD34+CD9−CD41$^{dim}$ cell population. C) Transposition of the CD34+CD9−CD41$^{dim}$ population on the CD34/CD41 graph in the cell suspension on day 10 (as used for example in FIG. 3 for obtaining the CD34+CD41$^{dim}$ cell population). The circle in C) indicates the cell population CD34+CD9 CD41+ in said CD34/CD41 graph. Comparison with for example FIG. 3A (Day 10) demonstrates that said CD34+CD9−CD41. Cell population corresponds to the CD34+CD9 cell population as indicated in FIG. 3 with region R2.

EXAMPLE 1

Materials and Methods

Isolation of CD34+ Cells

CD34+ cells were recovered from leukodepletion filters obtained from the Etablissement Français du Sang-Alsace by adapting a procedure described by Ivanovic et al (Transfusion. 2006; 46:118-125.). Briefly, after 15 min incubation with RosetteSep® Human Granulocyte Depletion Cocktail (StemCell Technologies, Vancouver, Canada), mononuclear cells were isolated by Histopaque®-1077 (Sigma-Aldrich) density gradient separation for 30 min at 400 g. CD34+ cells were then isolated by positive selection using an immunomagnetic cell sorting system (AutoMacs, Miltenyi, Bergisch-Galdbach, Germany). A viability of 83.30±1.96% and a CD34+ purity of 82.80±2.25% were routinely obtained (n=6).

MK Differentiation in Culture

CD34+ cells were seeded in 48-well plates at a density of 4×10$^4$ per mL in StemSpan SFEM medium supplemented with 20 ng/mL human LDL and CC220 (1×), a cocktail of cytokines containing SCF, TPO, IL-6 and IL-9 (all from Stemcell Technologies), with or without addition of 1 µM SR1 (Cellagen Technology, San Diego, Calif.) (FIG. 1A). On day 7, the cells were harvested, washed and seeded at 5×10$^4$/mL in StemSpan SFEM medium containing 30 ng/mL TPO with or without 1 µM SR1 for an additional 7 days. The cultures were incubated at 37° C. under normoxic conditions and 5% CO$_2$. On days 7 and 10 of culture, the cells were counted, their viability was measured by propidium iodide exclusion in an automatic cell counter (ADAM, Digital-Bio, Korea) and the expression of CD34, CD41 and CD42b was analyzed in a Gallios flow cytometer using Kaluza software (Beckman Coulter, Villepinte, France). In some experiments, SR1 was replaced by the AhR agonist FICZ (Enzo life sciences, Villeurbane, France) added at 0.2 µM.

In a second protocol, CD34+ cells were cultured in the presence of mesenchymal stromal cells (MSCs) isolated from human bone marrow (Guilloton F et al., Blood. 2012; 119:2556-2567). MSCs were maintained in α-MEM medium supplemented with 10% fetal bovine serum (Invitrogen, Cergy Pontoise, France) and 2 ng/mL recombinant human (rh) FGF2 (Peprotech, Rocky Hill, N.J.). CD34+ cells were added to a confluent layer of MSCs at a density of 4×10$^4$/mL in 48-well plates in StemSpan SFEM medium supplemented with 20 ng/mL human LDL and CC220. On day 7, the cells in suspension were harvested, washed and co-cultured at 5×10$^4$/mL on a new layer of confluent MSCs in StemSpan SFEM medium containing 30 ng/mL TPO for an additional 7 days (FIG. 5A).

Cell Sorting

The cells recovered on day 10 were incubated with a mixture of Alexa-488-conjugated anti-CD41 (ALMA.17) and PE-Cy7-conjugated anti-CD34 mAbs (BD Biosciences) for 30 min at 4° C. They were then washed in PBS-EDTA and incubated for 30 min in PBS containing 7-AAD (1/50) to select viable cells. The morphologic and sorting gates were determined by FMO (fluorescence minus one) analysis and megakaryocytic precursors were sorted at 500 cells/s according to their CD34/CD41 expression using a FACS Aria II flow cytometer (Becton Dickinson, Mountain View, Calif.) equipped with a 50 µm nozzle and two argon lasers operating at 500 mW and tuned to 488 and 360 nm, respectively (Coherent Radiation, Palo Alto, Calif.). The sorted CD34+CD41$^{dim}$ and CD34 CD41+ cells were then counted and seeded at 4×10$^4$/mL in 48-well plates in StemSpan medium containing TPO with or without SR1 for 7 days (FIG. 4A).

Analysis of MK Maturation

Surface Markers. Cells were analyzed by flow cytometry (Gallios, Beckman Coulter, France) after labeling with anti-CD34-PE-Cy7 (Beckman Coulter, Fullerton, Calif.), anti-CD41-Alexa-488 (ALMA.17), anti-CD42c-PE (RAM.1) and anti-CD42d-Alexa-647 (V.1) mAbs for 30 min at 4° C. The cells were then washed and resuspended in PBS containing 7-AAD (1/50). The acquired data were analyzed with Kaluza software.

Ploidy. Cells were incubated for 2 h at 37° C. with 10 µg/mL Hoechst 33342 (Sigma-Aldrich, Saint Quentin Fallavier, France) and then stained with anti-CD34-PE-Cy7 and anti-CD41-PE mAbs. The washed cells were resuspended in PBS containing 7-AAD and the ploidy distribution in the CD41 population was determined by two-color flow cytometry (Fortessa, BD Biosciences, Rungis, France). The acquired data were analyzed with BD FACSDiva software (BD Biosciences).

Ultrastructure. Cells were fixed with 2.5% glutaraldehyde in 0.1 M cacodylate buffer, pH 7.2, containing 2% sucrose and processed as described previously (Eckly A et al., Blood. 2014; 123:921-930). Ultrathin sections were examined under a Philips CM120 Biotwin transmission electron microscope (FEI, Heindhoven, The Netherlands) at 120 kV.

Quantification of Proplatelet-Bearing MKs

The percentage of MKs extending proplatelets was determined in the culture wells by phase-contrast microscopy. In each culture, at least 100 MKs were analyzed and images were acquired using a Zeiss Axio Vert.A1 microscope with a 20× objective (Marly-le-Roi, France).

Determination of the Number of Platelets Produced Per Seeded Cell

CD34+ cells cultured for 7 days in the presence of CC220 (FIGS. 1A and 5A) or CD34/CD41 sorted cells (FIGS. 4A and 6A) were seeded in a medium containing TPO. On day 7, 1 µM $PGE_1$ and 0.02 U/mL apyrase were added to the culture medium and the cells were gently passed 5 times through a P1000 pipet tip. The resulting suspension (200 µL) was incubated with anti-CD41-Alexa-647 and anti-CD42c-Alexa-488 mAbs for 15 min at room temperature before analysis in a Gallios flow cytometer. CD41/CD42c double positive events, having the same scattering properties as washed blood platelets, were counted as platelet-like particles and the number of particles per seeded cell, at day 7 or 10 following experiments, was determined.

RNA Extraction

CD41/61 cells were obtained on day 7 or 10 of culture using the antibody ALMA.17 and magnetic beads (Easy-Sep® "Do-It-Yourself" Selection Kit, StemCell Technologies). Total RNA were extracted using an RNeasy® Mini kit (QIAGEN) following manufacturer's instructions. Quantity and quality of total RNA for all samples were evaluated by measuring OD at 260 nm and concentration was adjusted at 50 ng/ml. The RNA samples were stored at −80° C. until use. qRT-PCR was applied under standard conditions using the SYBR Green Master Mix kit on the ABI Prism 7900 Sequence Detection System (PerkinElmer-Cetus, Courtaboeuf, France). The primers for genes were chosen with the assistance of the Oligo 6.0 program (National Biosciences, Plymouth, Minn.) and have been previously described (Bieche I. et al., Pharmacogenetics and genomics. 2007; 17:731-742).

Statistics

Statistical significance was determined by means of Student's t-test or two-way Anova followed by a Bonferroni post-test. Data were analyzed using Graphpad Prism 5 software.

Results

SR1 Sustains CD34 Expression in MKs Differentiated from Peripheral Blood CD34+ Cells We evaluated the effect of the AhR antagonist SR1 on the expansion of MK precursors. SR1 (50 µM) was added on days 0 and 7 in a two-step culture protocol where peripheral blood CD34+ cells (Peytour Y et al., Transfusion. 2010; 50:2152-2157) were first expanded for 7 days in the presence of CC220, an optimized mix of SCF, TPO, IL-6 and IL-9, and then differentiated for a further 7 days in the presence of TPO alone (FIG. 1A).

Using this protocol more than 90% of the control cells, cultured without SR1, were double positive for the platelet markers CD41 and CD42 on day 12 and displayed the hallmark features of fully mature MKs in morphologic and phenotypic analyses.

Cell proliferation was estimated on days 7 and 10, before the occurrence of proplatelet extension. On day 7, there was a 6.7±1.6 fold and 4.2±1.2 fold expansion of the total nucleated cells (mean±SEM, n=8) in the absence and presence of SR1, respectively (FIG. 1B). From day 7 to day 10 the number of cells increased similarly, 2.3 and 2.5 times, in untreated and SR1-treated cultures, respectively. Therefore, SR1 did not promote cell proliferation under our culture conditions.

We then evaluated the effect of SR1 on the maintenance of progenitors by following the evolution of CD34 expression. CD34 positivity was preserved in control and SR1-treated cells during the expansion step, with only a 16.8 and 8.3% decrease in positivity on day 7, respectively (FIG. 1C). On day 10, following passage in the presence of TPO alone, the proportion of CD34+ cells dropped to 40.7% in control cultures whereas 71.6% remained positive after SR1 treatment. Thus, SR1 maintained a more progenitor-like phenotype following transfer of the cells into media containing only added TPO.

SR1 Increases the Production of Proplatelet-Bearing MKs and Platelet-Like Elements In control cultures, proplatelet extension was first observed on day 10 and culminated on day 14 when 11.5±4.5% of the MKs exhibited proplatelets (FIG. 2A). Remarkably, this proportion tripled after SR1 treatment (34.6±2.1%, mean±SEM, n=4) and this resulted in an increased production of platelet-like elements. Whereas under control conditions 7.92±3.25 platelet sized particles were counted per cell seeded on day 7 (FIG. 2B), the number of platelet particles increased about 3 fold after addition of SR1 (20.72±5.19). These results indicated that SR1 not only sustained progenitor potential but also greatly improved MK maturation. On the contrary, when SR1 was replaced by FICZ, a strong agonist of the AhR, there was a dramatic decrease in the proplatelet extension of MKs and the production of platelet-like elements (0.20±0.04 platelets/seeded cell). Such results strongly suggested that AhR blockade is at the origin of the increased platelet production in the presence of SR1. The antagonist activity of SR1 was confirmed on the inhibition of the expression of its downstream target CYP1B1 in a day 7 culture as measured by qPCR (579.8±40.8 vs 2.5±0.8 arbitrary units in control and SR1 treated cells, respectively; means±SEM, n=3).

SR1 Promotes the Expansion of a $CD34^+CD41^{dim}$ Population

The above findings pointed to a dual effect of SR1 as it sustained CD34 expression and also improved MK maturation. Since CD41 is a specific marker of MKs, we evaluated its evolution in parallel with that of CD34. On day 7, a similar high proportion of CD34+ cells had acquired CD41 positivity with respectively 60 and 69% of the cells being CD34+CD41+ in control and SR1-treated cultures (FIG. 3A). Passage in the presence of TPO alone led to a significant loss of CD34 positivity in control cultures, with only 32% of the cells being CD34+CD41+ on day 10. In contrast, a high proportion (55%) remained double positive for CD34 and CD41 in SR1-treated cultures. Remarkably, a large fraction of these cells (37% of the total cells vs 17% in controls) exhibited a $CD41^{dim}$ phenotype (region R2) (FIG. 3B). The $CD41^{dim}$ population ($R_2$) comprised cells of decreased size as compared to those with a higher level of CD41 ($R_1$), as evidenced by their FSC properties (FIG. 3C), indicating a lower degree of MK differentiation. This was confirmed by the ploidy analysis since $CD34^+CD41^{dim}$ cells were mostly 2n–4n (FIG. 4).

$CD34^+CD41^{dim}$ Cells have a High Capacity to Produce Proplatelets and Platelet-Like Particles Addition of SR1 in the two-step culture protocol resulted in an increased production of proplatelet-bearing MKs and platelet-like elements (FIG. 2A-B). We therefore investigated whether this was related to the expansion and particular properties of the $CD34^+CD41^{dim}$ population. $CD34^+CD41^{dim}$ cells from a day 10 culture with SR1 were sorted by flow cytometry and cultured for 7 days in a TPO-containing medium supplemented or not with SR1 (FIG. 5A). An unprecedented high proportion of MKs reached the proplatelet stage (91.0±2.4%) when $CD34^+CD41^{dim}$ cells were grown in the presence of SR1 (FIG. 4B). Much lower frequencies were observed when these same cells were cultured in the absence of SR1 (10.0±6.6%) (FIG. 5B). The increased proplatelet yield led to a 6.8 fold enhanced production of platelet-like elements in CD34$^+$CD41$^{dim}$ cells cultured with SR1 as compared to without SR1 (52.06±8.79 vs 7.68±0.81 platelets/seeded cell, respectively) (FIG. 5C). These results indicated that the CD34$^+$CD41$^{dim}$ population expanded in the presence of SR1 has a strong potential to produce proplatelet-bearing MKs which are prone to release platelets.

Co-Culture with MSCs Also Promotes the Emergence of a CD34$^+$CD41$^{dim}$ Population Bone marrow-derived stromal cells can maintain hematopoietic stemness, secrete cytokines and favor MK maturation (Pallotta I et al., PloSone. 2009; 4:e8359; Cheng L et al., Journal of cellular physiology. 2000; 184:58-69) and could provide a favorable milieu for the emergence of an MK precursor. CD34$^+$ cells were cultured in a two-step protocol on preformed monolayers of human mesenchymal stromal cells (hMSCs) isolated from human bone marrow (FIG. 6A). Co-culture with hMSCs did not significantly modify cell proliferation (FIG. 6B) but resulted in increased production of proplatelet-bearing MKs (data not shown) and platelet-like particles on day 14 (7.9±4.5 vs 18.2±4.9 platelets/cell seeded on day 7) (FIG. 6C).

We investigated whether the effects of MSCs might be mediated by a pathway downstream of the AhR. Addition of the AhR agonist FICZ (Boitano A E et al., Science. 2010; 329:1345-1348) reduced the proportion of CD34$^+$CD41$^{dim}$ cells (data not shown) and prevented the increase in platelet production (FIG. 7A). In addition, co-culture of CD34 cells with MSCs resulted in a profound decrease (>90%) in CYP1B1 transcripts, reproducing the effect of SR1 (FIG. 5E), an effect that was reversed by the addition of FICZ (FIG. 7B). These results indicated that MSCs similarly to SR1 promote MK maturation and platelet production by acting on the AhR.

This response resembled that obtained with SR1, which prompted us to determine the CD34/CD41 phenotype of the cells. A population with the CD34$^+$CD41$^{dim}$ profile was clearly apparent by day 10 of co-culture (FIG. 8A) and represented 30.37±1.98% of the total cells, as compared to 18.95±1.75% in control cultures without MSCs (FIG. 8B). This population was of low ploidy (FIG. 8C).

We then sought to determine whether i) MSC- and SR1-derived CD34$^+$CD41$^{dim}$ cells had the same potential to produce mature MKs and ii) co-culture with MSCs or in the presence of SR1 similarly favored this maturation. CD34$^+$ cells were cultured with SR1 or on MSCs and the corresponding CD34$^+$CD41$^{dim}$ cells were sorted on day 10 (FIG. 9). These cells were then subcultured for 7 days with TPO, with TPO and SR1 or with TPO and MSCs. The results showed that MSC-derived CD34$^+$CD41$^{dim}$ cells exhibited an increased capacity to produce proplatelet-bearing MKs when cultured in the presence of SR1 (FIG. 9A, left panel), but with lower efficiency than SR1-derived cells (FIG. 9B, left panel) (49.5±10.5% vs 91.0±2.4%, respectively, n=4). In addition, co-culture with MSCs enhanced the MK maturation of both MSC-derived (FIG. 9A) and SR1-derived (FIG. 9B) CD34$^+$CD41$^{dim}$ cells (53.3±10.7% vs 67.5±12.6%, respectively) compared to culture with TPO alone (%). Similar profiles were observed for the capacity to liberate platelet-like particles (FIGS. 9A-B, right panels). Thus, co-culture with MSCs phenocopied the responses obtained by adding SR1 to cell cultures.

Altogether, it is therein reported the identification and enrichment of a discrete population of adult hematopoietic progenitors primed for MK differentiation which can efficiently mature to proplatelet-bearing MKs. This population, identified by means of its CD34$^+$CD41$^{dim}$ signature, was amplified when adult CD34$^+$ cells were cultured in the presence of SR1, an antagonist of the AhR, or an MSC monolayer. Culture with SR1 or MSCs, in addition to promoting the appearance of this MK progenitor, greatly improved the yield of proplatelet-producing MKs and the release of platelet-like elements.

Several features of the CD34$^+$CD41$^{dim}$ population identified here in the human system, such as the small size and low ploidy of the cells and their high capacity to mature into pure MKs able to efficiently extend proplatelets, appear to correspond to the definition of a platelet-biased progenitor. Its distinctive phenotype combines a CD34$^+$ progenitor signature with intermediate or dim expression of the CD41 megakaryocytic marker. CD41 positive cells have been described among human CD34$^+$ cells isolated directly from bone marrow or after culture under MK promoting conditions (Debili N. et al., Blood. 1992; 80:3022-3035; Dercksen M W et al., Blood. 1995; 86:3771-3782). However, these populations did not fully recapitulate the CD34$^+$CD41$^{dim}$ phenotype since they appeared to express higher levels of CD41 and were highly polyploid and unable to proliferate (Dercksen M W et al., Blood. 1995; 86:3771-3782). CD34$^+$CD41$^+$ cells have also been observed after co-culture of bone marrow-derived CD34$^+$ cells on hMSCs without TPO, but no evidence was provided for a distinct CD41$^{dim}$ subpopulation (Cheng L. et al., Journal of cellular physiology. 2000; 184:58-69). Cells with a CD34$^+$CD41$^{low}$ phenotype representing a very minor population were recently reported in cultures derived from peripheral blood but were not characterized further. The CD34$^+$CD41$^{dim}$ population was similarly of low frequency in our standard cultures (FIG. 3A) and only became apparent upon addition of SR1 or co-culture with MSCs. A CD31$^+$CD34$^+$CD41$^+$ megakaryoblastic population resembling the cells described here was recently observed in reprogrammed iPS cells cultured in a three-step serum-free system. This population appeared to express low levels of CD41 and was negative for CD42.

EXAMPLE 2

Materials and Methods

Peripheral blood CD34$^+$ cells were isolated as described above in the section "Isolation of CD34$^+$ cells" and cultured in the presence of SR1 (1 µM) as described above in the section "MK differentiation in culture" of example 1.

The cells recovered on day 10 were incubated with a mixture of Alexa-488-conjugated anti-CD41 (ALMA.17), phycoerythrin (PE)-Cy7-conjugated anti-CD34 monoclonal antibodies and phycoerythrin (PE)-CD9 (mAbs; BD Biosciences) for 30 minutes at 4° C. They were then incubated for 2 minutes in phosphate-buffered saline containing 7-aminoactinomycin D (2.5 µg/mL) to select viable cells.

The cells were first subdivided into CD34$^+$CD9$^-$ progenitors. Cell sorting using CD9$^-$ excludes CD41$_{high}$ cells because only CD9+ cells are CD4$_{high}$ as shown in FIG. 11. The population of CD34$^+$CD9$^-$ progenitor cells (which thus does not comprise CD41$^{high}$ cells) was then fractionated into MK progenitors according to the FSC/CD41$^+$ expression. The only CD41$^+$ present in the cell population are CD41$^{dim}$ therefore allowing to gate on the population of interest of CD34$^+$CD9$^-$CD41$^{dim}$ cells. Megakaryocytic precursors were then sorted at 500 cells/s using a fluorescence-activated cell sorter (FACS) Aria II flow cytometer (Becton Dickinson, Mountain View, Calif.). The sorted CD34$^+$CD9$^-$ CD41$^{dim}$ cells were then counted and seeded at 4×10$^4$/mL in 48-well plates in StemSpan medium containing TPO, with or without SR1, for 7 days.

Results

The population previously described as being CD34$^+$CD41$^{dim}$ can be also characterized as CD34$^+$CD9$^-$CD41$^{dim}$. In particular, CD34$^+$CD9$^-$CD41$^{dim}$ represents a subpopulation of CD34$^+$CD41$^{dim}$, wherein the population CD34$^+$CD9$^-$CD41$^{dim}$ represents 60% of the total population of CD34$^+$CD41$^{dim}$ cells. The differentiation potential of CD34$^+$CD41$^{dim}$ cells compared to CD34$^+$CD9$^-$CD41$^{dim}$ cells was functionally examined. CD34$^+$CD9$^-$CD41$^{dim}$ cells have a platelet release that is increased by 1.8 fold compared to CD34$^+$CD41$^{dim}$ cells.

The invention claimed is:

1. An ex vivo method of producing proplatelet-bearing megakaryocytes (MKs) and/or platelets comprising:
   a) culturing an isolated CD34$^+$CD9$^-$CD41$^+$ cell population of MK progenitors in a serum-free culture medium comprising thrombopoietin (TPO), in presence of an aryl hydrocarbon receptor (AhR) antagonist or by co-culture with human mesenchymal stromal cells (hMSCs), for a time sufficient to obtain a cell population comprising proplatelet-bearing MKs and/or platelets; and
   b) collecting said cell population comprising proplatelet-bearing MKs and/or platelets.

2. The method according to claim 1, wherein in a), culturing is conducted for 5 to 9 days.

3. The method according to claim 1, wherein the serum-free culture medium comprises 20-100 ng/ml TPO.

4. The method according to claim 1, wherein said method comprises, prior to a):
   a0) culturing haematopoietic stem cells (HSC) in a serum-free culture medium comprising low-density lipoprotein (LDL), stem cell factor (SCF), TPO, IL-6 and IL-9, in presence of an aryl hydrocarbon receptor (AhR) antagonist or by co-culture with human mesenchymal stromal cells (hMSCs), for a time sufficient to obtain a cell population comprising CD34$^+$CD9$^-$CD41$^+$ cells; and
   a1) isolating said CD34$^+$CD9$^-$CD41$^+$ cells from said cell population.

5. The method according to claim 4, wherein the serum-free culture medium of a0) comprises 10-30 μg/ml LDL, 25-100 ng/ml SCF, 40-50 ng/ml TPO, 20-30 ng/ml IL-6 and 20-30 ng/ml IL-9.

6. The method according to claim 4, wherein in a0), culturing is conducted for 6 to 8 days.

7. The method according to claim 1, wherein in a) and a0), independently, the AhR antagonist is a compound of formula (I)

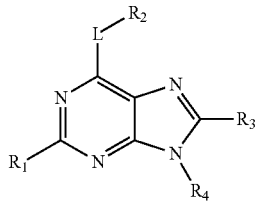

L is selected from the group consisting of —NR$_{5a}$(CH$_2$)$_{2-3}$-, —NR$_{5a}$(CH$_2$)$_2$NR$_{5b}$—, —NR$_{5a}$(CH$_2$)$_2$S—, —NR$_{5a}$CH$_2$CH(OH)— and —NR$_{5a}$CH(CH$_3$)CH$_2$—; wherein R$_{5a}$ and R$_{5b}$ are independently hydrogen or C$_{1-4}$alkyl;

R$_1$ is selected from the group consisting of thiophenyl, furanyl, benzoimidazolyl, isoquinolinyl, imidazopyridinyl, benzothiophenyl, pyrimidinyl, pyrazolyl, pyridinyl, imidazolyl, pyrrolidinyl, pyrazinyl, pyridazinyl, pyrrolyl and thiazolyl; wherein said thiophenyl, furanyl, benzoimidazolyl, isoquinolinyl, imidazopyridinyl, benzothiophenyl, pyrimidinyl, pyrazolyl, pyridinyl, imidazolyl, pyrrolidinyl, pyrazinyl, pyridazinyl, pyrrolyl and thiazolyl of R$_1$ is optionally substituted by 1 to 3 radicals independently selected from the group consisting of halo, cyano, C$_{1-4}$alkyl, halo-substituted-C$_{1-4}$alkyl, C$_{1-4}$alkoxy, —S(O)$_{0-2}$R$_{8a}$, and —C(O)OR$_{8a}$, wherein R$_{8a}$ is hydrogen or C$_{1-4}$alkyl;

R$_2$ is selected from the group consisting of —S(O)$_2$NR$_{6a}$R$_{6b}$, —NR$_{6a}$C(O)NR$_{6b}$R$_{6c}$, phenyl, pyrrolopyridinyl, indolyl, thiophenyl, pyridinyl, triazolyl, 2-oxoimidazolidinyl, pyrazolyl, and indazolyl; wherein R$_{6a}$, R$_{6b}$ and R$_{6c}$ are independently hydrogen or C$_{1-4}$alkyl; and said phenyl, pyrrolopyridinyl, indolyl, thiophenyl, pyridinyl, triazolyl, oxoimidazolidinyl, pyrazolyl, or indazolyl of R$_2$ is optionally substituted with 1 to 3 radicals independently selected from the group consisting of hydroxy, halo, methyl, methoxy, amino, —O(CH$_2$)$_n$NR$_{7a}$R$_{7b}$, —OS(O)$_2$NR$_{7a}$R$_{7b}$ and —NR$_{7a}$S(O)$_2$R$_{7b}$; wherein R$_{7a}$ and R$_{7b}$ are independently hydrogen or C$_{1-4}$alkyl;

R$_3$ is selected from the group consisting of hydrogen, C$_{1-4}$alkyl and biphenyl; and R$_4$ is selected from the group consisting of C$_{1-10}$alkyl, C$_{1-4}$alkenyl, oxetanyl, tetrahydrofuranyl, cyclohexyl, (oxopyrrolidinyl)ethyl, tetrahydropyranyl, phenyl, and benzyl, wherein said C$_{1-10}$alkyl, C$_{1-4}$alkenyl, oxetanyl, tetrahydrofuranyl, cyclohexyl, (oxopyrrolidinyl)ethyl, tetrahydropyranyl, phenyl, and benzyl of R$_4$ can be optionally substituted with 1 to 3 radicals independently selected from the group consisting of hydroxy, C$_{1-4}$alkyl and halo-substituted-C$_{1-4}$alkyl.

8. The method according to claim 1, wherein in a), the AhR antagonist is StemRegenin 1 (SR1).

9. The method according to claim 1, wherein a) is performed by co-culture with hMSCs.

10. The method according to claim 7 wherein said hMSCs are obtained by a method comprising:
   i) isolating bone marrow mononuclear cells (BM-MNCs) from a human subject by Ficoll density gradient;
   ii) seeding isolated BM-MNCs in culture medium comprising 5-15% fetal bovine serum and 0.5-5 ng/mL fibroblast growth factor 2 (FGF-2);
   iii) culturing seeded cells for two days, and the discarding nonadherent cells and seeding collected adherent cells;
   iv) culturing adherent cells in culture medium comprising 10% fetal bovine serum and 0.5-5 ng/mL FGF-2, with replacement of culture medium twice a week with fresh culture medium until confluence; and
   v) harvesting hMSCs, seeding and culturing harvested cells until confluence in culture medium comprising 10% fetal bovine serum and 0.5-5 ng/mL FGF-2.

11. The method according to claim 1, which further comprises selecting CD41/CD61+ and CD42c+ cells from the collected cell population comprising proplatelet-bearing MKs and/or platelets.

12. The method according to claim 1, which further comprises washing the proplatelet-bearing megakaryocytes (MKs) and/or platelets and suspending the washed cells in an infusion buffer.

13. A method of producing megakaryocyte (MK) progenitor cells comprising:
   a0) culturing haematopoietic stem cells (HSC) in a serum-free culture medium comprising low-density lipoprotein (LDL), stem cell factor (SCF), TPO, IL-6 and IL-9, in presence of an aryl hydrocarbon receptor (AhR) antagonist or by co-culture with human mesenchymal stromal cells (hMSCs), for a time sufficient to obtain a cell population comprising $CD34^+CD9^-CD41^+$ cells; and
   a1) isolating said $CD34^+CD9^-CD41^+$ cells from said cell population.

14. The method according to claim 4, wherein in a) and/or a0), the AhR antagonist is StemRegenin 1 (SR1).

15. The method according to claim 4, wherein a) and/or a0) is performed by co-culture with hMSCs.

* * * * *

UNITED STATES PATENT AND TRADEMARK OFFICE
CERTIFICATE OF CORRECTION

PATENT NO. : 11,236,303 B2
APPLICATION NO. : 15/747023
DATED : February 1, 2022
INVENTOR(S) : Strassel et al.

It is certified that error appears in the above-identified patent and that said Letters Patent is hereby corrected as shown below:

On the Title Page

Item (73):
Please change:
"**Assignees:
INSTITUT NATIONAL DE LA SANTE ET DE LA RECHERCHE MEDICALE (INSERM), Paris (FR); ETABLISSMENT FRANçIS DU SANG, La Plaine Saint Denis (FR); UNIVERSITÉ DE STRASBOURG**, Strasbourg (FR)"
To:
"**Assignees:
INSTITUT NATIONAL DE LA SANTE ET DE LA RECHERCHE MEDICALE (INSERM), Paris (FR); ETABLISSEMENT FRANÇAIS DU SANG, La Plaine Saint Denis (FR); UNIVERSITÉ DE STRASBOURG**, Strasbourg (FR)"

Signed and Sealed this
Eighteenth Day of October, 2022

Katherine Kelly Vidal
*Director of the United States Patent and Trademark Office*